US012708600B2

(12) United States Patent
Viravau et al.

(10) Patent No.: US 12,708,600 B2
(45) Date of Patent: Aug. 18, 2026

(54) COSMETIC COMPOSITION COMPRISING AN AMINO SILICONE, A NON-AMINO SILICONE AND A NON-IONIC ASSOCIATIVE POLYMER, AND COSMETIC TREATMENT PROCESS

(71) Applicant: L'OREAL, Paris (FR)

(72) Inventors: Valérie Viravau, Saint-Ouen (FR); Laurent Chesneau, Saint-Ouen (FR)

(73) Assignee: L'Oréal, Paris (FR)

( * ) Notice: Subject to any disclaimer, the term of this patent is extended or adjusted under 35 U.S.C. 154(b) by 429 days.

(21) Appl. No.: 18/255,297

(22) PCT Filed: Dec. 8, 2021

(86) PCT No.: PCT/EP2021/084741
§ 371 (c)(1),
(2) Date: May 31, 2023

(87) PCT Pub. No.: WO2022/135927
PCT Pub. Date: Jun. 30, 2022

(65) Prior Publication Data

US 2024/0115486 A1 Apr. 11, 2024

(30) Foreign Application Priority Data

Dec. 21, 2020 (FR) ...................................... 2013797

(51) Int. Cl.

| | |
|---|---|
| ***A61K 8/34*** | (2006.01) |
| ***A61K 8/06*** | (2006.01) |
| ***A61K 8/58*** | (2006.01) |
| ***A61K 8/73*** | (2006.01) |
| ***A61K 8/86*** | (2006.01) |
| ***A61K 8/87*** | (2006.01) |
| ***A61K 8/891*** | (2006.01) |
| ***A61K 8/898*** | (2006.01) |
| ***A61K 8/90*** | (2006.01) |
| ***A61Q 5/12*** | (2006.01) |

(52) U.S. Cl.
CPC .............. *A61K 8/898* (2013.01); *A61K 8/062* (2013.01); *A61K 8/585* (2013.01); *A61K 8/731* (2013.01); *A61K 8/737* (2013.01); *A61K 8/891* (2013.01); *A61K 8/90* (2013.01); *A61Q 5/12* (2013.01); *A61K 2800/5422* (2013.01); *A61K 2800/594* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 4,131,576 | A | 12/1978 | Iovine et al. | |
| 4,137,180 | A | 1/1979 | Naik et al. | |
| 4,874,554 | A | 10/1989 | Lange et al. | |
| 4,957,732 | A | 9/1990 | Grollier et al. | |
| 2004/0163187 | A1* | 8/2004 | Cottard .................... | A61K 8/87 8/405 |
| 2013/0129648 | A1 | 5/2013 | Nguyen et al. | |
| 2016/0008242 | A1* | 1/2016 | Schmenger .............. | A61Q 5/08 8/406 |
| 2017/0027851 | A1* | 2/2017 | Ran .......................... | A61K 8/34 |
| 2018/0133135 | A1 | 5/2018 | Scheele et al. | |
| 2020/0268621 | A1* | 8/2020 | Roy ........................ | A61K 8/416 |
| 2024/0115486 | A1 | 4/2024 | Viravau et al. | |

FOREIGN PATENT DOCUMENTS

| | | | |
|---|---|---|---|
| EP | 0186507 | A2 | 7/1986 |
| EP | 2883533 | A1 | 6/2015 |
| FR | 3058639 | A1 | 5/2018 |
| GB | 2540236 | A | 1/2017 |
| JP | H11209247 | A | 8/1999 |
| JP | 2003231617 | A | 8/2003 |
| JP | 2008110938 | A | 5/2008 |
| KR | 102114084 | B1 | 5/2020 |
| KR | 20200052700 | A | 5/2020 |
| WO | 2006/040286 | A1 | 4/2006 |
| WO | 2015/158499 | A1 | 10/2015 |
| WO | 2017/021444 | A1 | 2/2017 |
| WO | 2017117522 | A1 | 7/2017 |
| WO | 2018064677 | A1 | 4/2018 |
| WO | 2020/061658 | A1 | 4/2020 |

OTHER PUBLICATIONS

Office Action in CN202180083966.4, mailed Feb. 18, 2025, 21 pages.

International Search Report and Written Opinion for counterpart Application No. PCT/EP2021/084700, dated Mar. 10, 2022.

International Search Report and Written Opinion for counterpart Application No. PCT/EP2021/084741, dated Mar. 10, 2022.

Copending U.S. Appl. No. 18/255,297, entitled: "Cosmetic Composition Comprising a Silicone, a Starch and at Least 3% of Polyol, and Cosmetic Treatment Process," inventors: Laurent Chesneau et al., filed May 23, 2023.

Davies, J.T., "A Quantitative Kenetic Theory of Emulsion Type. I. Physical Chemistry of the Emulsifying Agent," Reprinted from: Gas/Liquid and Liquid/Liquid Interfaces, Proceedings of 2nd International Congress Surfact Activity, Butterworths, London, 1957, pp. 426-438.

Fonnum, G., et al., "Associative Thickeners. Part I: Synthesis, Rheology and Aggregation Behavior," Colloid Polym. Sci., 271, (1993) pp. 380-389.

Godfrey, K.M., "Cationic Emulsifiers in Cosmetics," J. Soc. Cosmetic Chemists, 17, (1966), pp. 17-27.

(Continued)

*Primary Examiner* — Brian Gulledge

(74) *Attorney, Agent, or Firm* — The Marbury Law Group, PLLC

(57) ABSTRACT

The present invention relates to a cosmetic composition, preferably a hair composition, comprising one or more amino silicones, one or more non-amino silicones and one or more non-ionic associative polymers. The invention also relates to a cosmetic treatment process for keratin materials, in particular for caring for and/or conditioning the hair, using said cosmetic composition.

19 Claims, No Drawings

(56) References Cited

OTHER PUBLICATIONS

Griffin, William C., “Calculation of HLB Values of Non-Ionic Surfactants,” J. Soc. Cosmet. Chemists, vol. 5 (1954), pp. 249-256.
Noll, Walter, “Chemistry and Technology of Silicones,” Academic Press, New York, San Francisco, London, 1968, pp. 1-23.
Puisieux, F., et al., Galencia 5: Les systèmes dispersés—Tome 1—Agents de surface et emulsions—Chapitre IV—Notions de HLB et du HLB critique,pp. 153-194—paragraph 1.1.2 Détermination de HLB par voie expérimental [Experimental determination of HLB], pp. 164-180.
Todd, Charles, et al., “Volatile Silicone Fluids for Cosmetic Formulations,” Cosmetics and Toiletries, vol. 91, Jan. 1976, pp. 29-32.
Office Action in U.S. Appl. No. 18/254,064, mailed Feb. 11, 2026, 8 pages.
Office Action in U.S. Appl. No. 18/254,064, mailed Aug. 20, 2025, 9 pages.

* cited by examiner

COSMETIC COMPOSITION COMPRISING AN AMINO SILICONE, A NON-AMINO SILICONE AND A NON-IONIC ASSOCIATIVE POLYMER, AND COSMETIC TREATMENT PROCESS

CROSS REFERENCE TO RELATED APPLICATIONS

This is a National Stage Application of PCT/EP2021/084741, filed internationally on Dec. 8, 2021, which claims priority to French Application No. 2013797, filed Dec. 21, 2020, both of which are incorporated by reference herein in their entireties.

The present invention relates to a cosmetic composition, in particular a hair composition, comprising one or more amino silicones, one or more non-amino silicones, and one or more non-ionic associative polymers; and a cosmetic treatment process, in particular for the hair, using said composition.

Hair can be damaged and embrittled by the action of external atmospheric agents such as light and bad weather, and/or by mechanical or chemical treatments, such as brushing, combing, dyeing, bleaching, permanent-waving and/or relaxing, or even repeated washes.

Hair is thus damaged by these various factors and may over time become dry, coarse, brittle or dull, in particular in fragile areas, such as at the ends.

To overcome these drawbacks, it is common practice to resort to haircare treatments using compositions that condition the hair, giving it satisfactory cosmetic properties, notably in terms of smoothness, sheen, softness, suppleness, lightness, a natural feel and good disentangling properties. These haircare compositions intended to be applied regularly to the hair may be, for example, hair conditioners, masks or serums, and may be in the form of gels, hair lotions or care creams that are more or less thick.

The products present on the market generally have a thick texture and can be difficult to apply and to spread uniformly over the entire head of hair. The use of these products can therefore be optimized to provide a more pleasant sensory experience.

The objective of the present invention is to provide hair compositions which are easy to use, in particular which are easy to apply and spread on the hair, and which melt there quickly, by virtue of the flexible, thickened, or even gelled, particularly melting texture of the composition, said texture gliding on the strand of hair and being easy to spread; a composition is also sought which is easily rinsed off without leaving residues, and which will provide the hair with good sensory and care properties such as instant disentangling, a soft and smooth feel, and also affording light and supple hair.

A subject of the present invention is thus a cosmetic composition, notably a hair composition, comprising:

(i) one or more amino silicones, (ii) one or more non-amino silicones, and (iii) one or more non-ionic associative polymers.

A subject of the invention is also a process for cosmetic treatment, in particular cosmetic hair treatment, of keratin materials, in particular keratin fibres such as the hair, comprising the application to said keratin materials of a composition as defined in the present description.

The composition according to the invention has good working qualities (in particular capture, application, distribution, absorption on the hair), and in particular an adequate viscosity which enables it to be applied and to be spread easily and quickly over the head of hair. Moreover, it is very easy to rinse off. It advantageously has a smooth cream texture, and a shiny appearance, with a consistency allowing easy capture, in particular when the composition is packaged in a jar.

Advantageously, the composition according to the invention has a viscosity, measured at 25° C. and 1 atm, ranging from 200 to 10 000 cps (0.2 to 10 Pa·s), preferably from 500 to 8000 cps (0.5 to 8 Pa·s), preferentially from 800 to 5000 cps (0.8 to 5 Pa·s), even better still from 1000 to 3000 cps (1 to 3 Pa·s).

The viscosity may be measured using a Rheomat RM180 machine at 25° C. and 1 atm, with a 3 spindle, the spin speed being 200 rpm and the measuring time 30 seconds. In addition, the composition according to the invention gives keratin fibres good cosmetic properties, such as a smooth and very soft feel, and also light, supple, shiny, very clean hair. The keratin fibres are also easy to disentangle and are not made heavy by the composition.

Other characteristics, aspects and advantages of the invention will become even more clearly apparent on reading the description and the examples which follow.

In the text which will follow, and unless otherwise indicated, the limits of a range of values are included in this range, especially in the interchangeable expressions "of between" and "ranging from . . . to . . . ".

The expression "at least one" used in the present description is equivalent to the expression "one or more".

In the present description, the term "silicone" is in particular intended to mean, in accordance with what is generally accepted, any organosilicon polymer or oligomer of linear or cyclic, branched or crosslinked structure, of variable molecular weight, obtained by polymerization and/or polycondensation of suitably functionalized silanes, and formed essentially from a repetition of main units in which the silicon atoms are linked together via oxygen atoms (siloxane bond —Si—O—Si—), optionally substituted hydrocarbon-based groups being directly linked via a carbon atom to said silicon atoms. The hydrocarbon-based groups that are the most common are alkyl groups, notably $C_1$-$C_{10}$ alkyl groups and in particular methyl, fluoroalkyl groups, the alkyl part of which is $C_1$-$C_{10}$, and aryl groups and in particular phenyl.

The weight-average molecular weights (Mw) of the (amino or non-amino) silicones may be measured by gel permeation chromatography (GPC) at ambient temperature (25° C.), as polystyrene equivalent. The columns used are μ styragel columns. The eluent is THF and the flow rate is 1 ml/minute. 200 μl of a 0.5% by weight solution of silicone in THF are injected. Detection is performed by refractometry and UV-metry.

A/ Amino Silicones

The composition according to the invention comprises one or more amino silicones.

The term "amino silicone" denotes any silicone comprising at least one primary, secondary or tertiary amine or a quaternary ammonium group.

The amino silicones that may be used according to the present invention can be volatile or non-volatile, cyclic, linear or branched, and preferably have a viscosity ranging from $5\times10^{-6}$ to 2.5 $m^2/s$ at 25° C., for example from $1\times10^{-5}$ to 1 $m^2/s$.

Preferably, the amino silicone(s) are chosen from:

A) the polysiloxanes corresponding to formula (I):

(I)

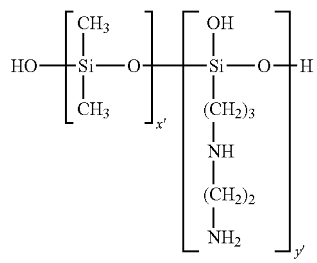

in which x' and y' are integers such that the weight-average molecular weight (Mw) is between 5000 and 500 000 g/mol;

B) the amino silicones corresponding to formula (II):

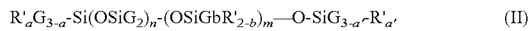

$$R'_aG_{3-a}\text{-Si}(OSiG_2)_n\text{-}(OSiG_bR'_{2-b})_m\text{—O-Si}G_{3-a'}\text{-}R'_{a'} \quad (II)$$

in which:

G, which may be identical or different, denotes a hydrogen atom or a phenyl, OH, $C_1$-$C_8$ alkyl, for example methyl, or $C_1$-$C_8$ alkoxy, for example methoxy, group, a and a', which may be identical or different, denote 0 or an integer from 1 to 3, in particular 0, with the proviso that at least one from among a and a' is equal to zero, b denotes 0 or 1, in particular 1, m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10; and R', which may be identical or different, denotes a monovalent radical of formula $—C_qH_{2q}L$ in which q is a number ranging from 2 to 8 and L is an optionally quaternized amino group chosen from the following groups: $—NR''\text{-}Q\text{-}N(R'')_2$, $—N(R'')_2$, $—N^+(R'')_3\ A^-$, $—N^+H(R'')_2\ A^-$, $—N^+H_2(R'')\ A^-$, $—NR''\text{-}Q\text{-}N^+(R'')H_2\ A^-$, $—NR''\text{-}Q\text{-}N^+(R'')_2H\ A^-$ and $—NR''\text{-}Q\text{-}N^+(R'')_3\ A^-$, in which R'', which may be identical or different, denotes hydrogen, phenyl, benzyl, or a monovalent saturated hydrocarbon-based radical, for example a $C_1$-$C_{20}$ alkyl radical; Q denotes a linear or branched group of formula $C_rH_{2r}$, r being an integer ranging from 2 to 6, preferably from 2 to 4; and $A^-$ represents a cosmetically acceptable anion, in particular a halide, such as fluoride, chloride, bromide or iodide.

Preferably, the amino silicones of formula (II) can be chosen from:

(a) the "trimethylsilylamodimethicone" silicones corresponding to formula (III):

(III)

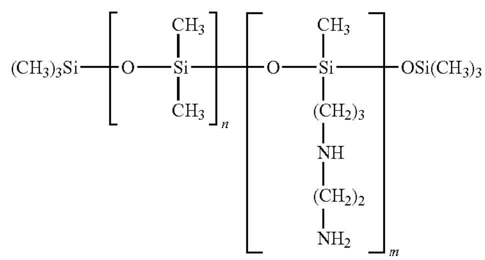

in which m and n are numbers such that the sum (n+m) ranges from 1 to 2000, preferably from 20 to 1000, in particular from 50 to 600, better still from 50 to 150; n possibly denoting a number from 0 to 1999 and especially from 49 to 149, and m possibly denoting a number from 1 to 2000 and especially from 1 to 10;

(b) the silicones of formula (IV) below:

(IV)

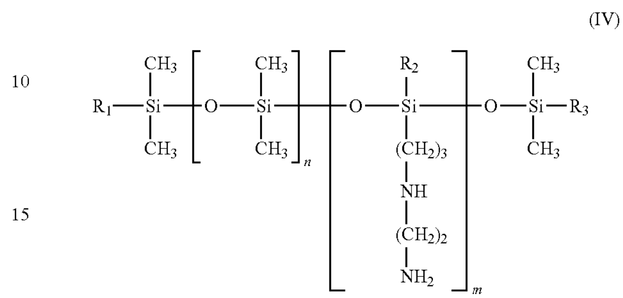

in which:

m and n are numbers such that the sum (n+m) ranges from 1 to 1000, in particular from 50 to 250 and more particularly from 100 to 200; n denoting a number from 0 to 999 and especially from 49 to 249 and more particularly from 125 to 175, and m denoting a number from 1 to 1000, especially from 1 to 10 and more particularly from 1 to 5; and $R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

Preferably, the alkoxy radical is a methoxy radical.

The hydroxy/alkoxy mole ratio preferably ranges from 0.2:1 to 0.4:1 and preferably from 0.25:1 to 0.35:1 and more particularly is equal to 0.3:1.

The weight-average molecular weight (Mw) of these silicones preferably ranges from 2000 to 1 000 000 g/mol and more particularly from 3500 to 200 000 g/mol;

(c) the silicones of formula (V) below:

(V)

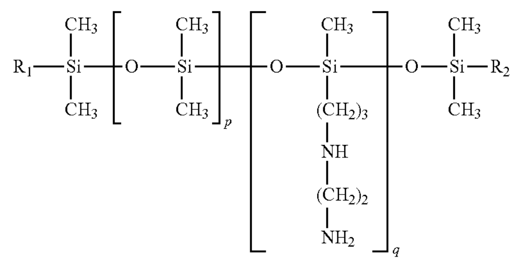

in which:

p and q are numbers such that the sum (p+q) ranges from 1 to 1000, in particular from 50 to 350 and more particularly from 150 to 250; p denoting a number from 0 to 999 and especially from 49 to 349 and more particularly from 159 to 239, and q denoting a number from 1 to 1000, especially from 1 to 10 and more particularly from 1 to 5; and $R_1$ and $R_2$, which are different, represent a hydroxyl or $C_1$-$C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly is equal to 1:0.95.

The weight-average molecular weight (Mw) of the silicone preferably ranges from 2000 to 200 000 g/mol, more preferentially from 5000 to 100 000 g/mol and in particular from 10 000 to 50 000 g/mol.

The commercial products comprising silicones of structure (IV) or (V) may include in their composition one or more other amino silicones, the structure of which is different from formula (IV) or (V). A product containing amino silicones of structure (IV) is sold by the company Wacker under the name Belsil® ADM 652. A product containing amino silicones of structure (V) is sold by Wacker under the name Fluid WR 1300@. Another product containing amino silicones of structure (IV) is sold by Wacker under the name Belsil ADM LOG 1®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or non-ionic. The number-average size of the silicone particles in the emulsion generally ranges from 3 nm to 500 nanometres. Preferably, notably as amino silicones of formula (V), use is made of microemulsions of which the mean particle size ranges from 5 nm to 60 nm (limits included) and more particularly from 10 nm to 50 nm (limits included). Thus, use may be made according to the invention of the microemulsions of amino silicone of formula (V) sold under the names Finish CT 96 E® or SLM 28020® by the company Wacker;

(d) the silicones of formula (VI) below:

(VI)

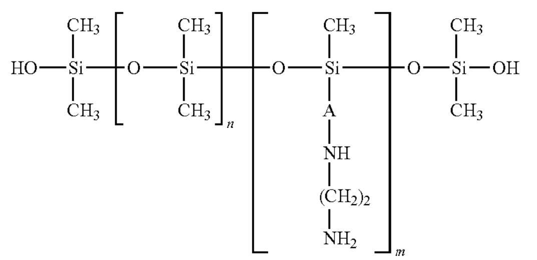

in which:

m and n are numbers such that the sum (n+m) ranges from 1 to 2000 and in particular from 50 to 150, n denoting a number from 0 to 1999 and especially from 49 to 149, and m denoting a number from 1 to 2000 and especially from 1 to 10; and A denotes a linear or branched alkylene radical having from 4 to 8 carbon atoms and preferably 4 carbon atoms. This radical is preferably linear.

The weight-average molecular weight (Mw) of these amino silicones preferably ranges from 2000 to 1 000 000 g/mol and more particularly from 3500 to 200 000 g/mol.

A silicone corresponding to this formula is, for example, Xiameter MEM 8299 Emulsion from Dow Corning;

(e) the silicones of formula (VII) below:

(VII)

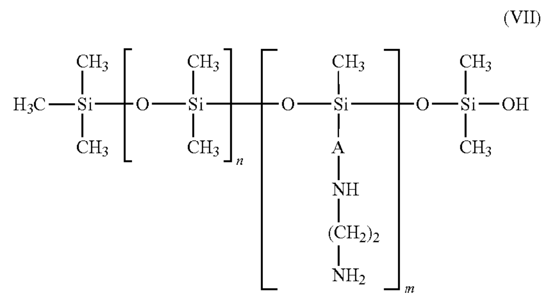

in which:

m and n are numbers such that the sum (n+m) ranges from 1 to 2000 and in particular from 50 to 150, n possibly denoting a number from 0 to 1999 and especially from 49 to 149, and m possibly denoting a number from 1 to 2000 and especially from 1 to 10; and A denotes a linear or branched alkylene radical having from 4 to 8 carbon atoms and preferably 4 carbon atoms. This radical is preferably branched.

The weight-average molecular mass (Mw) of these amino silicones preferably ranges from 500 to 1 000 000 g/mol and more particularly from 1000 to 200 000 g/mol.

A silicone corresponding to this formula is, for example, DC2-8566 Amino Fluid from Dow Corning;

C) the amino silicones corresponding to formula (VIII):

(VIII)

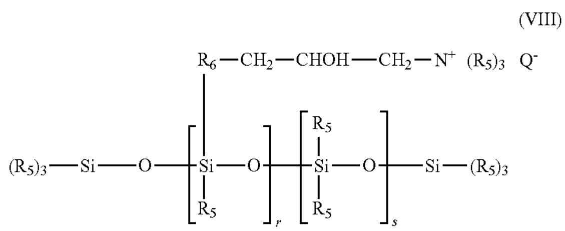

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

$Q^-$ is an anion such as a halide ion, in particular chloride, or an organic acid salt, in particular acetate;

r represents a mean statistical value ranging from 2 to 20 and in particular from 2 to 8;

and s represents a mean statistical value ranging from 20 to 200 and in particular from 20 to 50;

D) the quaternary ammonium silicones of formula (IX):

(IX)

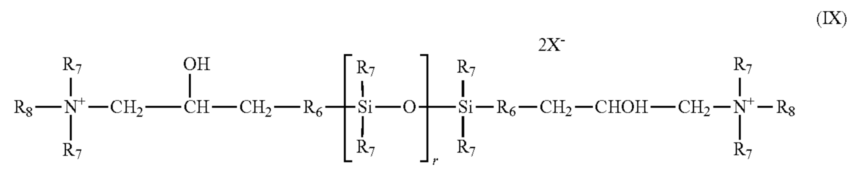

in which:

$R_7$, which may be identical or different, represent a monovalent hydrocarbon-based radical having from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represent a hydrogen atom, a monovalent hydrocarbon-based radical having from 1 to 18 carbon atoms, and in particular a $C_1$-$C_{18}$ alkyl radical, a $C_2$-$C_{18}$ alkenyl radical or a radical —$R_6$—$NHCOR_7$;

$X^-$ is an anion such as a halide ion, notably chloride, or an organic acid salt, notably acetate; and r represents a mean statistical value ranging from 2 to 200 and in particular from 5 to 100;

E) the amino silicones of formula (X):

(X)

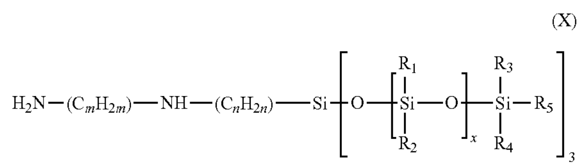

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and x is chosen such that the amine number ranges from 0.01 to 1 meq/g;

F) multiblock polyoxyalkylenated amino silicones, of the type (AB)n, A being a polysiloxane block and B being a polyoxyalkylenated block comprising at least one amine group, Said silicones are preferably constituted of repeating units having the following general formulae:

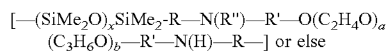

$[—(SiMe_2O)_xSiMe_2$-R—N(R'')—R'—$O(C_2H_4O)_a$ $(C_3H_6O)_b$—R'—N(H)—R—] or else

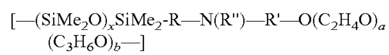

$[—(SiMe_2O)_xSiMe_2$-R—N(R'')—R'—$O(C_2H_4O)_a$ $(C_3H_6O)_b$—]

in which:

a is an integer greater than or equal to 1, preferably ranging from 5 to 200 and more particularly ranging from 10 to 100;

b is an integer between 0 and 200, preferably ranging from 4 to 100 and more particularly between 5 and 30;

x is an integer ranging from 1 to 10 000 and more particularly from 10 to 5000;

R'' is a hydrogen atom or a methyl;

R, which may be identical or different, represent a linear or branched divalent $C_2$-$C_{12}$ hydrocarbon-based radical, optionally comprising one or more heteroatoms such as oxygen; preferably, R, which may be identical or different, denote an ethylene radical, a linear or branched propylene radical, a linear or branched butylene radical or a $CH_2CH_2CH_2OCH_2CH(OH)CH_2$— radical; preferentially, R denote a $CH_2CH_2CH_2OCH_2CH(OH)CH_2$— radical; and R', which may be identical or different, represent a linear or branched divalent $C_2$-$C_{12}$ hydrocarbon-based radical, optionally comprising one or more heteroatoms such as oxygen; preferably, R', which may be identical or different, denote an ethylene radical, a linear or branched propylene radical, a linear or branched butylene radical or a $CH_2CH_2CH_2OCH_2CH(OH)CH_2$— radical; preferentially, R' denote —$CH(CH_3)$—$CH_2$—.

The siloxane blocks preferably represent between 50 mol % and 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably between 5000 and 1 000 000 g/mol and more particularly between 10 000 and 200 000 g/mol.

Mention may in particular be made of the silicones sold under the name Silsoft A-843 or Silsoft A+ by Momentive;

G) the amino silicones of formulae (XI) and (XII):

(XI)

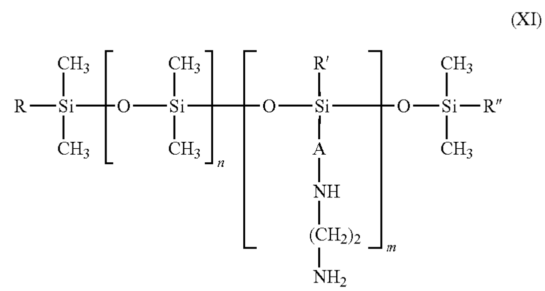

in which:

R, R' and R'', which may be identical or different, denote a $C_1$-$C_4$ alkyl group or a hydroxyl group, A denotes a $C_3$ alkylene radical; and m and n are numbers such that the weight-average molecular weight of the compound is between 5000 and 500 000;

(XII)

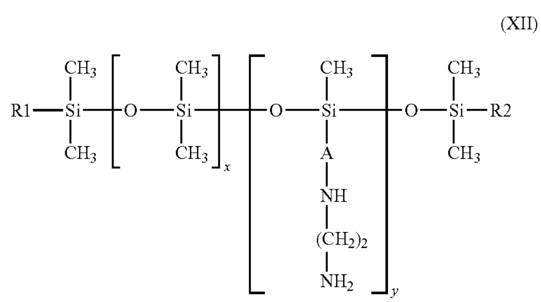

in which:

x and y are numbers ranging from 1 to 5000; preferably, x ranges from 10 to 2000 and more preferentially from 100 to 1000; preferably, y ranges from 1 to 100;

$R_1$ and $R_2$, which may be identical or different, preferably are identical, denote a linear or branched, saturated or unsaturated alkyl group comprising from 6 to 30 carbon atoms, preferably from 8 to 24 carbon atoms and more preferentially from 12 to 20 carbon atoms; and A denotes a linear or branched alkylene radical having from 2 to 8 carbon atoms.

Preferably, A comprises from 3 to 6 carbon atoms, more preferentially 4 carbon atoms; preferably, A is branched. Mention may be made in particular of the following divalent groups: $—CH_2CH_2CH_2—$ and $—CH_2CH(CH_3)CH_2—$.

Preferably, $R_1$ and $R_2$ are independent saturated linear alkyl groups comprising 6 to 30 carbon atoms, preferably 8 to 24 carbon atoms and in particular from 12 to 20 carbon atoms; mention may be made in particular of dodecyl, tetradecyl, pentadecyl, hexadecyl, heptadecyl, octadecyl, nonadecyl and eicosyl groups; and preferentially, R1 and R2, which may be identical or different, are chosen from hexadecyl (cetyl) and octadecyl (stearyl) groups.

Preferably, the silicone of formula (XII) has:

x ranging from 10 to 2000 and in particular from 100 to 1000;

y ranging from 1 to 100;

A comprising from 3 to 6 carbon atoms and in particular 4 carbon atoms; preferably, A is branched; more particularly, A is chosen from the following divalent groups: $—CH_2CH_2CH_2—$ and $—CH_2CH(CH_3)CH_2—$; and $R_1$ and $R_2$ independently being saturated linear alkyl groups comprising from 6 to 30 carbon atoms, preferably from 8 to 24 carbon atoms and in particular from 12 to 20 carbon atoms; chosen in particular from dodecyl, tetradecyl, pentadecyl, hexadecyl, heptadecyl, octadecyl, nonadecyl and eicosyl groups; preferentially, $R_1$ and $R_2$, which may be identical or different, being chosen from hexadecyl (cetyl) and octadecyl (stearyl) groups.

A silicone of formula (XII) that is preferred is bis-cetearyl amodimethicone. Mention may be made in particular of the amino silicone sold under the name Silsoft AX by Momentive;

H) polysiloxanes and notably polydimethylsiloxanes, including primary amine groups at only one chain end or on side chains, such as those of formula (XIV), (XV) or (XVI):

(XIV)

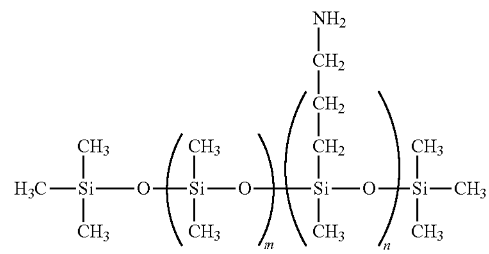

(XV)

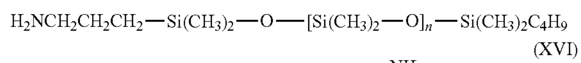

(XVI)

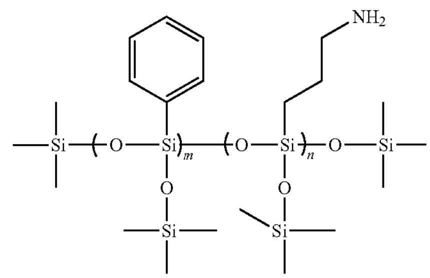

In formula (XIV), the values of n and m are such that the weight-average molecular weight of the amino silicone is between 1000 and 55 000.

As examples of amino silicones of formula (XIV), mention may be made of the products sold under the names AMS-132, AMS-152, AMS-162, AMS-163, AMS-191 and AMS-1203 by the company Gelest and KF-8015 by the company Shin-Etsu.

In formula (XV), the value of n is such that the weight-average molecular weight of the amino silicone is between 500 and 3000.

As examples of amino silicones of formula (XV), mention may be made of the products sold under the names MCR-A11 and MCR-A12 by the company Gelest.

In formula (XVI), the values of n and m are such that the weight-average molecular weight of the amino silicone is between 500 and 50 000.

As examples of amino silicones of formula (XVI), mention may be made of the aminopropyl phenyl trimethicone sold under the name DC 2-2078 Fluid by the company Dow Corning.

I) and mixtures thereof.

Preferably, the amino silicone(s) are chosen from the amino silicones of formula (III) and mixtures thereof, preferentially from the amino silicones of formula (III) in which m and n are numbers such that the sum (n+m) ranges from 20 to 100, in particular 50 to 600, better still 50 to 150; n possibly denoting a number from 49 to 149 and m possibly denoting a number from 1 to 10.

The composition according to the present invention may comprise the amino silicone(s) in a total content preferably ranging from 0.01% to 5% by weight, preferentially from 0.05% to 2% by weight, and more preferentially from 0.1% to 1% by weight, relative to the total weight of the composition.

Advantageously, the composition according to the present invention may comprise the amino silicone(s) of formula (III) in a total content preferably ranging from 0.01% to 5% by weight, preferentially from 0.05% to 2% by weight, and more preferentially from 0.1% to 1% by weight, relative to the total weight of the composition.

B/ Non-Amino Silicones

The composition according to the invention also comprises one or more non-amino silicones, which can be solid or liquid, preferably liquid (at 25° C., 1 atm), and volatile or non-volatile.

The silicones that may be used may be soluble or insoluble in the composition according to the invention; they may be in the form of oil, wax, resin or gum; silicone oils and gums are preferred.

Silicones are in particular described in detail in Walter Noll's *Chemistry and Technology of Silicones* (1968), Academic Press.

The volatile silicones may be chosen from those with a boiling point of between 60° C. and 260° C. (at atmospheric pressure) and in particular from:

i) cyclic polydialkylsiloxanes including from 3 to 7 and preferably 4 to 5 silicon atoms, such as

- octamethylcyclotetrasiloxane (D4) and decamethylcyclopentasiloxane (D5).

Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia.

- cyclocopolymers of the dimethylsiloxane/methylalkylsiloxane type having the chemical structure:

With D:

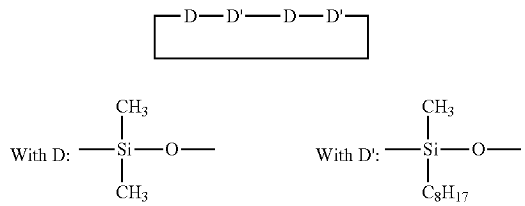

Mention may be made of Volatile Silicone FZ 3109 sold by the company Union Carbide;

- mixtures of cyclic silicones with silicon-based organic compounds, such as the mixture of octamethylcyclotetrasiloxane and of tetratrimethylsilylpentaerythritol (50/50) and the mixture of octamethylcyclotetrasiloxane and of oxy-1,1'-bis(2,2,2',2',3,3'-hexatrimethylsilyloxy)neopentane;

ii) linear polydialkylsiloxanes containing 2 to 9 silicon atoms, which generally have a viscosity of less than or equal to $5\times10^{-6}$ $m^2/s$ at 25° C., such as decamethyltetrasiloxane.

Other silicones belonging to this category are described in the article published in Cosmetics and Toiletries, Vol. 91, January 76, pages 27-32, Todd & Byers *Volatile Silicone Fluids for Cosmetics*; mention may be made of the product sold under the name SH 200 by the company Toray Silicone.

Among the non-volatile silicones, mention may be made, alone or as a mixture, of polydialkylsiloxanes and in particular polydimethylsiloxanes (PDMS or dimethicone), polydiarylsiloxanes, polyalkylarylsiloxanes, silicone gums and resins, and also non-amino organopolysiloxanes (or organomodified polysiloxanes, or alternatively organomodified silicones) which are polysiloxanes including in their structure one or more non-amino organofunctional groups, generally attached via a hydrocarbon-based group, and preferably chosen from aryl groups, alkoxy groups and polyoxyethylene or polyoxypropylene groups.

The organomodified silicones may be polydiarylsiloxanes, in particular polydiphenylsiloxanes, and polyalkylarylsiloxanes functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes including:

- polyoxyethylene and/or polyoxypropylene groups optionally including $C_6$-$C_{24}$ alkyl groups, such as dimethicone copolyols, and notably those sold by the company Dow Corning under the name DC 1248 or the oils Silwet® L 722, L 7500, L 77 and L 711 from the company Union Carbide; or alternatively ($C_{12}$)alkylmethicone copolyols, and notably those sold by the company Dow Corning under the name Q2-5200;
- thiol groups, such as the products sold under the names GP 72 A and GP 71 from Genesee;
- alkoxylated groups, such as the product sold under the name Silicone Copolymer F-755 by SWS Silicones and Abil Wax® 2428, 2434 and 2440 by the company Goldschmidt;
- hydroxylated groups, for instance polyorganosiloxanes bearing a hydroxyalkyl function;
- acyloxyalkyl groups, such as the polyorganosiloxanes described in U.S. Pat. No. 4,957,732;
- anionic groups of the carboxylic acid type, as described, for example, in EP 186 507, or of the alkylcarboxylic type, such as the product X-22-3701 E from the company Shin-Etsu; or else of the 2-hydroxyalkylsulfonate or 2-hydroxyalkylthiosulfate type, such as the products sold by the company Goldschmidt under the names Abil© S201 and Abil© S255;

The silicones may also be chosen from polydialkylsiloxanes, among which mention may be made mainly of polydimethylsiloxanes bearing trimethylsilyl end groups (CTFA: dimethicone). Among these polydialkylsiloxanes, mention may be made of the following commercial products:

- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC200 with a viscosity of 60 000 $mm^2/s$;
- the Viscasil® oils from General Electric and certain oils of the SF series (SF 96, SF 18) from General Electric.

Mention may also be made of polydimethylsiloxanes containing dimethylsilanol end groups (CTFA: dimethiconol) such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

Products that may be used more particularly in accordance with the invention are mixtures such as:

- mixtures formed from a polydimethylsiloxane with a hydroxy-terminated chain, or dimethiconol (CTFA), and from a cyclic polydimethylsiloxane, also known as cyclomethicone (CTFA), such as the product Q2-1401 sold by the company Dow Corning.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ $m^2/s$ at 25° C.

Among these polyalkylarylsiloxanes, mention may be made of the products sold under the following names:

- the Silbione® oils of the 70 641 series from Rhodia;
- the oils of the Rhodorsil® 70 633 and 763 series from Rhodia;
- the Dow Corning 556 Cosmetic Grade Fluid oil from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

The non-amino silicones more particularly preferred according to the invention are polydimethylsiloxanes containing trimethylsilyl end groups (CTFA: dimethicone).

The cosmetic composition according to the invention may comprise the non-amino silicone(s) in a total amount preferably ranging from 0.1% to 10% by weight, better still from 0.2% to 5% by weight, or even from 0.5% to 2% by weight, relative to the total weight of the composition.

Advantageously, the cosmetic composition according to the invention can comprise the polydimethylsiloxane(s) containing trimethylsilyl end groups in a total amount preferably ranging from 0.1% to 10% by weight, better still from 0.2% to 5% by weight, or even from 0.5% to 2% by weight, relative to the total weight of the composition.

In one preferred embodiment, the composition according to the invention can comprise an oil-in-water emulsion comprising both the non-amino silicone(s) and the amino silicone(s).

In particular, the composition according to the invention can comprise an oil-in-water emulsion having a particle size D50 of less than 350 nm, and comprising:

- a silicone mixture comprising (i) a polydialkylsiloxane comprising trialkylsilyl end groups, having a viscosity at 25° C. ranging from 40 000 to 100 000 mPa·s and (ii) an amino silicone having a viscosity at 25° C. ranging from 1000 to 15 000 mPa·s and an amine number ranging from 2 to 10 mg of KOH per gram of amino silicone;
- a surfactant mixture comprising one or more non-ionic surfactants, said mixture having an HLB ranging from 10 to 16, and
- water.

In the oil-in-water, or silicone-in-water, emulsion according to the invention, a liquid phase (the dispersed phase) is advantageously dispersed in another liquid phase (the continuous phase); in the present invention, the mixture of silicones, or silicone phase, is dispersed in the aqueous continuous phase.

The mixture of silicones (or silicone mixture) can comprise one or more polydialkylsiloxanes comprising trialkylsilyl end groups, preferably of formula (I): R'3SiO(R'2SiO)pSiR'3 in which:

- R', which is identical or different, is a monovalent hydrocarbon-based radical having from 1 to 18 carbon atoms, preferably from 1 to 6 carbon atoms, better still from 1 to 3 carbon atoms, even better still a methyl radical, and
- p is an integer ranging from 500 to 2000, better still from 1000 to 2000.

The polydialkylsiloxanes containing trialkylsilyl end groups according to the invention have a viscosity ranging from 40 000 to 100 000 mPa·s (preferably 100 000 excluded) at 25° C., preferably ranging from 40 000 to 70 000 mPa·s at 25° C., better still from 51 000 to 70 000 mPa·s at 25° C.

The polydialkylsiloxanes comprising trialkylsilyl end groups according to the invention are preferably linear, but they may comprise, in addition to the $R'_2SiO_{2/2}$ units (D-units), additional $RSiO_{3/2}$ units (T-units) and/or $SiO_{4/2}$ units (Q-units), in which R', which is identical or different, is a C1-C18 monovalent hydrocarbon-based radical.

Preferably, in formula (I), R', which is identical or different, is:

- an alkyl, preferably C1-C28 alkyl, radical, such as the radicals methyl, ethyl, n-propyl, isopropyl, 1-n-butyl, 2-n-butyl, isobutyl, tert-butyl, n-pentyl, isopentyl, neopentyl, tert-pentyl, hexyl and in particular n-hexyl, heptyl and in particular n-heptyl, octyl and in particular n-octyl, isooctyl, 2,2,4-trimethylpentyl; nonyl and in particular n-nonyl; decyl and in particular n-decyl; dodecyl and in particular n-dodecyl; octadecyl and in particular n-octadecyl;
- an alkenyl radical such as vinyl and allyl;
- a cycloalkyl radical such as cyclopentyl, cyclohexyl, cycloheptyl and methylcyclohexyl;
- an aryl radical such as phenyl, naphthyl, anthryl and phenanthryl;
- an alkaryl radical such as the radicals o-, m- and p-tolyl; xylyl, ethylphenyl;
- an aralkyl radical such as benzyl and phenylethyl.

Preferentially, R' is a methyl radical.

Preferably, the polydialkylsiloxanes comprising trialkylsilyl end groups are polydimethylsiloxanes (PDMSs) comprising trialkylsilyl end groups.

The silicone mixture also comprises one or more amino silicones, preferably of formula (II): $XR_2Si(OSiAR)_n(OSiR_2)_mOSiR_2X$ in which:

- R, which is identical or different, is a monovalent hydrocarbon-based radical having from 1 to 18 carbon atoms, preferably from 1 to 6 carbon atoms, better still from 1 to 3 carbon atoms, even better still a methyl radical,
- X, which is identical or different, represents R or a hydroxyl (OH) or a C1-C6 alkoxy group; preferably X is R, that is to say a monovalent hydrocarbon-based radical having from 1 to 18 carbon atoms, preferably from 1 to 6 carbon atoms, better still from 1 to 3 carbon atoms, even better still a methyl radical,
- A is an amino radical of formula $—R^1—[NR^2—R^3—]_xNR^{22}$, or the protonated form of this amino radical, with
- $R^1$ representing a $C_1$-$C_6$ alkylene radical, preferably a $—CH_2CH_2CH_2—$ or $—CH_2CH(CH_3)CH_2—$ radical,
- $R^2$, which is identical or different, being a hydrogen atom or a $C_1$-$C_4$ alkyl radical, preferably a hydrogen atom,
- $R^3$ being a $C_1$-$C_6$ alkylene radical, preferably a $—CH_2CH_2—$ radical,
- x is 0 or 1;
- m and n are integers such that m+n ranges from 50 to 1000, better still from 50 to 600.

Preferably, A is an amino radical of formula $—R^1—[NR^2—R^3—]_xNR^{22}$, or the protonated form of this amino radical, with $R^1$ being $—CH_2CH_2CH_2—$ or $—CH_2CH(CH_3)CH_2—$, $R^2$ being hydrogen atoms, $R^3$ being $—CH_2CH_2—$ and x being equal to 1.

Preferably, R, which is identical or different, is:

- an alkyl, preferably C1-C28 alkyl, radical, such as the radicals methyl, ethyl, n-propyl, isopropyl, 1-n-butyl, 2-n-butyl, isobutyl, tert-butyl, n-pentyl, isopentyl, neopentyl, tert-pentyl, hexyl and in particular n-hexyl, heptyl and in particular n-heptyl, octyl and in particular n-octyl, isooctyl, 2,2,4-trimethylpentyl; nonyl and in particular n-nonyl; decyl and in particular n-decyl; dodecyl and in particular n-dodecyl; octadecyl and in particular n-octadecyl;

an alkenyl radical such as vinyl and allyl;

a cycloalkyl radical such as cyclopentyl, cyclohexyl, cycloheptyl and methylcyclohexyl;

an aryl radical such as phenyl, naphthyl, anthryl and phenanthryl;

an alkaryl radical such as the radicals o-, m- and p-tolyl; xylyl, ethylphenyl;

an aralkyl radical such as benzyl and phenylethyl.

Preferentially, R is a methyl radical.

The amino silicones of the emulsion according to the invention preferably have a viscosity at 25° ranging from 1000 to 15 000 mPa·s, preferably from 1500 to 15 000 mPa·s.

The amino silicones of the emulsion according to the invention preferably have an amine number ranging from 2 to 10 mg of KOH per gram of amino silicone; preferably from 3.5 to 8 mg.

The molar percentage of amine function is preferably between 0.3 and 8 mol %.

As examples of amino silicones, mention may be made of amino silicones comprising trialkylsilyl end groups; preferably aminoethylaminopropylmethylsiloxanes comprising trialkylsilyl end groups, even better still copolymers of aminoethylaminopropylmethylsiloxane comprising trialkylsilyl end groups/dimethylsiloxane.

The amino radical A may be partially or totally protonated, for example by addition of acids to the amino silicone, so as to obtain the salified form of said amino radical. As acids that may be used, mention may be made of linear or branched carboxylic acids having from 3 to 18 carbon atoms, such as formic acid, acetic acid, propionic acid, butyric acid, pivalic acid, sorbic acid, benzoic acid or salicylic acid. Preferably, the acids may be used in a proportion of from 0.1 to 2.0 mol per mole of amino radical A in the amino silicone of formula (II).

The silicone mixture preferably comprises (i) one or more polydialkylsiloxanes comprising trialkylsilyl end groups, having a viscosity, at 25° C., ranging from 40 000 to 100 000 mPa·s, in an amount of from 70% to 90% by weight, preferably from 75% to 85% by weight, and (ii) one or more amino silicones having a viscosity, at 25° C., ranging from 1000 to 15 000 mPa·s and an amine number ranging from 2 to 10 mg of KOH per gram of amino silicone, in an amount of from 10% to 30% by weight, in particular from 15% to 25% by weight, relative to the total weight of the silicone mixture.

The oil-in-water emulsion also comprises a surfactant mixture which comprises one or more non-ionic surfactants; said surfactant mixture may optionally comprise one or more cationic surfactants. Said surfactant mixture has an HLB ranging from 10 to 16.

The non-ionic surfactants that may be used may be chosen from alcohols, α-diols and (C1-C20)alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or else these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—(C6-C24 alkyl)glucamine derivatives, amine oxides such as (C10-C14 alkyl)amine oxides or N—(C10-C14 acyl)aminopropylmorpholine oxides.

Mention may also be made of non-ionic surfactants of alkyl(poly)glycoside type, represented in particular by the following general formula: $R_1O—(R_2O)_t(G)_v$ in which:

$R_1$ represents a linear or branched alkyl or alkenyl radical comprising 6 to 24 carbon atoms and especially 8 to 18 carbon atoms, or an alkylphenyl radical of which the linear or branched alkyl radical comprises 6 to 24 carbon atoms and especially 8 to 18 carbon atoms;

$R_2$ represents an alkylene radical comprising from 2 to 4 carbon atoms,

G represents a sugar unit comprising from 5 to 6 carbon atoms, t denotes a value ranging from 0 to 10, preferably from 0 to 4, v denotes a value ranging from 1 to 15, preferably from 1 to 4.

Preferably, the alkyl(poly)glycoside surfactants are compounds of the formula described above in which:

$R_1$ denotes a saturated or unsaturated and linear or branched alkyl radical comprising from 8 to 18 carbon atoms, $R_2$ represents an alkylene radical comprising from 2 to 4 carbon atoms, t denotes a value ranging from 0 to 3, preferably equal to 0, G denotes glucose, fructose or galactose, preferably glucose, the degree of polymerization, that is to say the value of v, being able to range from 1 to 15, preferably from 1 to 4; the mean degree of polymerization more particularly being of between 1 and 2.

The glucoside bonds between the sugar units are generally of 1-6 or 1-4 type, preferably of 1-4 type. Preferably, the alkyl(poly)glycoside surfactant is an alkyl(poly)glucoside surfactant. $C_8/C_{16}$ alkyl (poly)glucosides of 1-4 type, and in particular decyl glucosides and caprylyl/capryl glucosides, are very particularly preferred.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or the products sold by the company Chem Y under the name AG10 LK.

Preferably, use is made of C8/C16alkyl (poly)glycosides of 1-4 type, in particular as an aqueous 53% solution, such as those sold by Cognis under the reference Plantacare® 818 UP.

The mono- or polyglycerolated surfactants preferably comprise an average number of glycerol groups ranging from 1 to 30, especially from 1 to 10, better still from 1.5 to 5. They preferably correspond to one of the following formulae:

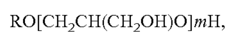
$RO[CH_2CH(CH_2OH)O]mH$,

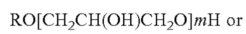
$RO[CH_2CH(OH)CH_2O]mH$ or

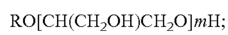
$RO[CH(CH_2OH)CH_2O]mH$;

in which:

R represents a saturated or unsaturated, linear or branched hydrocarbon-based (especially alkyl or alkenyl) radical including 8 to 40 carbon atoms, especially 10 to 30 carbon atoms, optionally comprising one or more heteroatoms such as 0 and N; and m is an integer ranging from 1 to 30, preferably from 1 to 10, better still from 1.5 to 6.

In particular, R may comprise one or more hydroxyl and/or ether and/or amide groups. Preferably, R is a mono- or polyhydroxylated C10-C20 alkyl or alkenyl radical. Mention may be made of polyglycerolated (3.5 mol) hydroxylauryl ether, such as the product Chimexane® NF from Chimex.

Mention may also be made of (poly)ethoxylated fatty alcohols preferably comprising one or more saturated or unsaturated, linear or branched hydrocarbon-based chains comprising 8 to 30 carbon atoms, preferably from 12 to 22 carbon atoms, optionally substituted with one or more hydroxyl (OH) groups, in particular 1 to hydroxyl groups. When the chain is unsaturated, it may comprise one to three conjugated or non-conjugated carbon-carbon double bonds.

The (poly)ethoxylated fatty alcohols preferably correspond to formula (II): R3-(OCH2CH2)cOH in which:

R3 represents a linear or branched alkyl or alkenyl radical comprising from 8 to 40 carbon atoms and in particular 8 to 30 carbon atoms, optionally substituted with one or more, in particular 1 to 4, hydroxyl groups; and c is an integer ranging from 1 to 200, in particular from 2 to 150, or even from 4 to 50 and even better still from 8 to 30.

The (poly)ethoxylated fatty alcohols are more particularly fatty alcohols comprising from 8 to 22 carbon atoms, oxyethylenated with 1 to 30 mol of ethylene oxide (1 to 30 EO); mention may in particular be made of lauryl alcohol 2 EO; lauryl alcohol 3 EO; decyl alcohol 3 EO; decyl alcohol 5 EO and oleyl alcohol 20 EO.

The non-ionic surfactants may advantageously be chosen from:

(i) (poly)oxyalkylenated, in particular (poly)ethoxylated, fatty alcohols, and in particular those of formula: $R3-(OCH_2CH_2)_cOH$ in which:

R3 represents a linear or branched alkyl or alkenyl radical comprising from 8 to 40 carbon atoms and in particular 8 to 30 carbon atoms, optionally substituted with one or more, in particular 1 to 4, hydroxyl groups; and c is an integer ranging from 1 to 200, in particular from 2 to 150, or even from 4 to 50 and even better still from 8 to 20.

(ii) (poly)oxyalkylenated (C8-C32)alkyl phenyl ethers, in particular comprising from 1 to 200, better still from 1 to 30 mol of ethylene oxide;

(iii) polyoxyalkylenated esters of C8-C32 fatty acids and of sorbitan, in particular polyoxyethylenated esters of C8-C32 fatty acids and of sorbitan, preferably having from 2 to 40 ethylene oxide units, better still from 2 to 20 ethylene oxide (EO) units; in particular polyoxyethylenated esters of C10-C24 fatty acids and of sorbitan, preferably having from 2 to 40 ethylene oxide units, better still from 2 to 20 ethylene oxide (EO) units; and (iv) polyoxyethylenated esters of C8-C32 fatty acids, preferably having from 2 to 150 ethylene oxide units; in particular polyoxyethylenated esters of C10-C24 fatty acids, comprising in particular 2 to 150 ethylene oxide (EO) units.

The non-ionic surfactants may advantageously be chosen from alkyl ethers and alkyl esters of polyalkylene glycol, especially of polyethylene glycol.

Mention may in particular be made of:

polyethylene glycol octyl ether; polyethylene glycol lauryl ether; polyethylene glycol tridecyl ether; polyethylene glycol cetyl ether; polyethylene glycol stearyl ether; and most particularly trideceth-3, trideceth-10 and steareth-6;

polyethylene glycol nonylphenyl ether; polyethylene glycol dodecylphenyl ether; polyethylene glycol cetylphenyl ether; polyethylene glycol stearylphenyl ether;

polyethylene glycol sorbitan monostearate, polyethylene glycol sorbitan monooleate;

polyethylene glycol stearate, and in particular PEG100 stearate.

Even better still, the non-ionic surfactants may be chosen from Steareth-6, PEG100 stearate, trideceth-3 and trideceth-10, and mixtures thereof; most particularly, a mixture comprising these four non-ionic surfactants.

The surfactant mixture may optionally comprise one or more cationic surfactants, which may be chosen from tetraalkylammonium, tetraarylammonium and tetraalkylaryl-lammonium salts, especially halides, and most particularly from cetrimonium or behentrimonium salts, in particular halides, better still chlorides.

The oil-in-water emulsion preferably comprises the surfactant mixture in a total amount ranging from 5% to 15% by weight, especially from 8% to 15% by weight, even better still from 10% to 12% by weight, relative to the total weight of the emulsion.

The oil-in-water emulsion preferably comprises the non-ionic surfactant(s) in a total amount ranging from 5% to 15% by weight, especially from 8% to 15% by weight, even better still from 10% to 12% by weight, relative to the total weight of the emulsion.

The oil-in-water emulsion preferably comprises the cationic surfactant(s), when they are present, in a total amount ranging from 0.5% to 1.5% by weight relative to the total weight of the emulsion.

The oil-in-water emulsion preferably comprises the silicone mixture in a total amount ranging from 40% to 60% by weight, especially from 45% to 55% by weight, relative to the total weight of the emulsion.

The oil-in-water emulsion preferably comprises the polydialkylsiloxane(s) comprising trialkylsilyl end groups in a total amount ranging from 35% to 45% by weight, especially from 38% to 42% by weight, relative to the total weight of the emulsion.

The oil-in-water emulsion preferably comprises the amino silicone(s) in a total amount ranging from 5% to 15% by weight, in particular from 8% to 12% by weight, relative to the total weight of the emulsion.

The oil-in-water emulsion preferably comprises water in a total amount ranging from 25% to 50% by weight, especially from 30% to 45% by weight, even better still from 35% to 42% by weight, relative to the total weight of the emulsion.

The oil-in-water emulsion may also comprise a preservative, such as phenoxyethanol, in an amount ranging from 0.5% to 1% by weight relative to the total weight of the emulsion.

A process for preparing the oil-in-water emulsion preferably comprises:

- a step of mixing one or more polydialkylsiloxanes containing trialkylsilyl end groups, having a viscosity, at 25° C., ranging from 40 000 to 100 000 mPa·s, and one or more amino silicones having a viscosity, at 25° C., ranging from 1000 to 15 000 mPa·s and an amine number ranging from 2 to 10 mg of KOH per gram of amino silicone; at a temperature of from 15° C. to 40° C., in particular at 25° C., in order to obtain a fluid mixture of silicones; then
- a step of adding a surfactant mixture comprising one or more non-ionic surfactants, said mixture having an HLB ranging from 10 to 16, to said fluid mixture of silicones, in order to obtain an emulsified silicone mixture; then
- a step of homogenizing said emulsified silicone mixture, followed by
- a step of adding water, especially demineralized water, preferentially in steps, in order to obtain an oil-in-water emulsion having a particle size D50 of less than 350 nm.

The preparation process may also comprise an additional step of adding one or more preservatives.

The pH of the oil-in-water emulsion is generally between 4 and 6.

The oil-in-water emulsion has a particle size D50 of less than 350 nm, especially of between 100 and 300 nm, better still between 150 and 250 nm, or even between 160 and 200 nm.

This size corresponds to the average hydrodynamic particle diameter. The particle size D50 is expressed by volume. It can be measured using a ZetaSizer device from Malvern, UK, model Nano-ZS, based on the "Photon Correlation Spectroscopy (PCS)" method.

Method for Measuring the Particle Size

The particle size of the emulsion is measured using a ZetaSizer device from Malvern, UK, model Nano-ZS, based on the "Photon Correlation Spectroscopy (PCS)" method. The particle size D50 is measured when the evaluation algorithm is "cumulant analysis". 0.5 g of the emulsion is placed in a 250 ml beaker, 100 ml of demineralized water are added and mixing is carried out in order to obtain the solution to be tested. The solution to be tested is placed in the measuring vessel (or cell) and introduced into the measuring device.

The size D50 corresponds to the particle diameter value at 50% in cumulative distribution.

For example, if $D_{50}$=170 nm, this means that 50% of the particles have a size of greater than 170 nm, and that 50% of the particles have a size of less than 170 nm.

It should be recalled that this distribution is by volume.

Method for Measuring the Viscosity

The viscosities, especially of the silicone compounds, are measured at 25° C., 1 atm.

To measure viscosities of between 1000 and 40 000 mPa·s at 25° C., use may be made of an Anton Paar rheometer, model MCR101, cylinder geometry, single gap: CC27 spindle, shear rate 1 $s^{-1}$ for 2 minutes, at 25° C.

To measure viscosities of between 40 000 and 100 000 mPa·s at 25° C., use may be made of an Anton Paar rheometer, model MCR101, 25-6 cone (cone-plate geometry, 25 mm in diameter/6° cone); Zero gap, shear rate 1 $s^{-1}$ for 2 minutes, at 25° C.

Three measurements are carried out for each sample, and the viscosity value is taken at 60 seconds. The MCR Rheometer Series products operate according to the USP convention (US Pharmacopeia Convention, 912—Rotational Rheometer methods).

Method for Measuring the Amine Number

The amine number can be measured by acid-base titration, using a potentiometer [Make: Veego; model VPT-MG].

0.6 g of the sample is placed in a 500 ml beaker and a 1:1 toluene-butanol mixture is added, then mixing is carried out.

The solution is titrated with a 0.1 N HCl solution. A determination of the zero value ($V_{blank}$) is also carried out with the 1:1 toluene-butanol mixture alone.

The amine number is calculated by means of the formula:

$$56.11\times(V-V_{Blank})\times N/W \text{ mg KOH/g of sample}$$

with V=volume of HCl required (in ml), $V_{Blank}$=volume of HCl required for the zero value (in ml); N=normality of HCl, i.e. 0.1, and W=weight of the sample (in g).

HLB Values

The term HLB relates to the hydrophilic-lipophilic balance of a surfactant. It can be measured experimentally or calculated.

In the present application, the HLB values are the values at 25° C.

The HLB values can be calculated by means of the following equation: HLB=(E+P)/5, in which E is the % by weight of oxyethylene and P is the % by weight of polyol, as is described in the publication Griffin, J. Soc. Cosm. Chem. 1954 (vol. 5, No. 4), pages 249-256.

The HLB values can also be determined experimentally according to the book by Puisieux and Seiller, entitled "Galenica 5: Les systèmes disperses [Galenica 5: Dispersed systems]—Volume I—Agents de surface et émulsions [Surface agents and emulsions]—Chapter IV—Notions de HLB et de HLB critique [Notions of HLB and of critical HLB], pages 153-194—paragraph 1.1.2. Détermination de HLB par voie expérimentale [Experimental determination of HLB], pages 164-180".

Preferably, the HLB values that will be taken into account are those obtained by calculation, especially in the following way: "calculated HLB"=20×(molar mass of the hydrophilic part/total molar mass).

Thus, for an oxyethylenated fatty alcohol, the hydrophilic part corresponds to the oxyethylene units fused to the fatty alcohol and the "calculated HLB" then corresponds to the "HLB according to Griffin".

For an ester or an amide, the hydrophilic part is generally defined as being beyond the carbonyl group, starting from the fatty chain(s).

The HLB values of non-ionic surfactants can also be calculated by means of the Davies formula, as described in Davies JT (1957), "A quantitative kinetic theory of emulsion type, I. Physical chemistry of the emulsifying agent", Gas/Liquid and Liquid/Liquid Interface (Proceedings of the International Congress of Surface Activity): 426-438.

According to this formula, the HLB value is obtained by adding the hydrophilic/hydrophobic contribution linked to the constituent groups in the surfactant: HLB=(number of hydrophilic groups)−n(number of groups per $CH_2$ group)+7.

The HLB values of some cationic surfactants are given in Table IV, in "Cationic emulsifiers in cosmetics", GODFREY, J. Soc. Cosmetic Chemists (1966) 17, pages 17-27.

When two surfactants A and B, of known HLB values, are mixed, the $HLB_{Mix}$ corresponds to the HLB of the mixture and can be expressed by the following equation: $HLB_{Mix}=(W_AHLB_A+W_BHLB_B)/(W_A+W_B)$ in which $W_A$ is the amount (weight) of the $1^{st}$ surfactant A and $W_B$ the amount of the $2^{nd}$ surfactant B, and $HLB_A$ and $HLB_B$ are the HLB values of the surfactant A and of the surfactant B.

According to this embodiment, preferably, the composition according to the invention comprises the oil-in-water emulsion in a total amount ranging from 0.1% to 10% by weight, better still from 0.2% to 8% by weight, preferentially from 0.5% to 6% by weight, relative to the total weight of the composition; preferably, the emulsion has a solids (or active material) content of between 40% and 60% by weight, in particular 45% to 55% by weight, relative to the total weight of the emulsion.

C/ Non-Ionic Associative Polymer

The composition according to the invention comprises one or more non-ionic associative polymers.

Optionally, it may also comprise one or more anionic or cationic associative polymers, alone or as a mixture.

For the purposes of the present invention, the term "associative polymer" is intended to mean an amphiphilic polymer that is capable, in an aqueous medium, of reversibly combining with itself or with other molecules. It generally comprises, in its chemical structure, at least one hydrophilic region or group and at least one hydrophobic region or group.

The term "hydrophobic region or group" is intended to mean a hydrocarbon-based group or a polymer, comprising a saturated or unsaturated, linear or branched hydrocarbon-based chain. When it denotes a hydrocarbon-based group, the hydrophobic group comprises at least 8 carbon atoms, preferably at least 10 carbon atoms, more preferably from 8 to 30 carbon atoms, in particular from 10 to 30 carbon atoms and preferentially from 10 to 24 carbon atoms. Preferentially, the hydrophobic group is derived from a monofunctional compound. By way of example, the hydrophobic group may be derived from a fatty alcohol, such as stearyl alcohol, dodecyl alcohol or decyl alcohol, or else from a polyoxyalkylenated fatty alcohol, such as steareth-100. It may also denote a hydrocarbon-based polymer, for instance polybutadiene.

The term "fatty chain" is intended hereinafter to mean a saturated or unsaturated, linear, branched or cyclic hydrocarbon-based chain, preferably a saturated, linear or branched (alkyl) hydrocarbon-based chain comprising at least 8 carbon atoms, preferably at least 10 carbon atoms, more preferably from 8 to 30 carbon atoms, in particular from 10 to 30 carbon atoms and preferentially from 10 to 24 carbon atoms.

The non-ionic associative polymers that may be used in the invention are preferably chosen from:

(1) celluloses modified with groups comprising at least one fatty chain. Mention may be made, by way of example, of:
   - hydroxyethylcelluloses modified with groups comprising at least one fatty chain, such as alkyl, arylalkyl or alkylaryl groups, or mixtures thereof, and in which the alkyl groups are preferably $C_8$-$C_{22}$ alkyl groups, such as the products Natrosol Plus Grade 330 CS ($C_{16}$ alkyls) or Polysurf 67 CS sold by Ashland, or the product Bermocoll EHM 100 sold by Berol Nobel,
   - hydroxyethylcelluloses modified with polyalkylene glycol ($C_8$-$C_{22}$ alkyl) phenyl ether groups, such as the product Amercell Polymer HM-1500 (nonylphenyl polyethylene glycol (15) ether) sold by Amerchol;

(2) hydroxypropyl guars modified with groups comprising at least one fatty chain, such as the product Esaflor HM 22 ($C_{22}$ alkyl chain), sold by Lamberti, and the products RE210-18 ($C_{14}$ alkyl chain) and RE205-1 ($C_{20}$ alkyl chain), sold by Rhodia Chimie;

(3) inulins modified with groups comprising at least one fatty chain, such as inulin alkyl carbamates and in particular the inulin lauryl carbamate provided by Orafti under the name Inutec SPI;

(4) copolymers of vinylpyrrolidone and of fatty-chain hydrophobic monomers, of which mention may be made, by way of example, of:
   - the products Antaron V216 or Ganex V216 (vinylpyrrolidone/hexadecene copolymer), sold by ISP,
   - the products Antaron V220 or Ganex V220 (vinylpyrrolidone/eicosene copolymer), sold by ISP;

(5) copolymers of $C_1$-$C_6$ alkyl methacrylates or acrylates and of amphiphilic monomers comprising at least one fatty chain, optionally oxyalkylated, for instance the oxyethylenated methyl acrylate/stearyl acrylate copolymer such as the one sold by the company Goldschmidt under the name Antil 208;

(6) copolymers of hydrophilic methacrylates or acrylates and of hydrophobic monomers comprising at least one fatty chain, such as, for example, the polyethylene glycol methacrylate/lauryl methacrylate copolymer;

(7) polyurethane polyethers comprising, in their chain, both hydrophilic blocks usually of polyoxyethylenated nature and hydrophobic blocks which can be aliphatic sequences alone and/or cycloaliphatic and/or aromatic sequences;

(8) polymers comprising an aminoplast ether backbone having at least one fatty chain, such as the Pure Thix compounds offered by Süd-Chemie.

Preferably, the non-ionic associative polyurethane polyethers according to the invention comprise at least two lipophilic hydrocarbon-based chains having from 8 to carbon atoms which are separated by a hydrophilic block, it being possible for the hydrocarbon-based chains to be pendent chains or chains at the end of the hydrophilic block. In particular, it is possible for one or more pendent chains to be envisaged. In addition, the polymer may include a hydrocarbon-based chain at one end or at both ends of a hydrophilic block.

The polyurethane polyethers may be multiblock, in particular in triblock form. The hydrophobic blocks may be at each end of the chain (for example: triblock copolymer bearing a hydrophilic central block) or distributed both at the ends and in the chain (for example, multiblock copolymer). These same polymers may also be graft polymers or star polymers.

The non-ionic fatty-chain polyurethane polyethers may be triblock copolymers, the hydrophilic block of which is a polyoxyethylene chain including from 50 to 1000 oxyethylene groups. The non-ionic polyether polyurethanes comprise a urethane linkage between the hydrophilic blocks, whence arises the name.

By extension, the non-ionic fatty-chain polyurethane polyethers also include those with hydrophilic blocks bonded to the lipophilic blocks via other chemical bonds.

Mention may also be made, as examples of non-ionic fatty-chain polyurethane polyethers that may be used in the invention, of Rheolate 205 comprising a urea function, sold by Elementis, or else Rheolate 208, 204 or 212, and also Acrysol RM 184.

Mention may also be made of the product Elfacos T210 containing a $C_{12}$-$C_{14}$ alkyl chain, and the product Elfacos T212 containing a $C_{18}$ alkyl chain, from Akzo.

The product DW 1206B from Röhm & Haas having a $C_{20}$ alkyl chain and a urethane bond, provided at a solids content of 20% in water, may also be used.

Use may also be made of solutions or dispersions of these polymers, notably in water or in aqueous-alcoholic medium. Mention may be made, as examples of such polymers, of Rheolate 255, Rheolate 278 and Rheolate 244, sold by Elementis. Use may also be made of the products DW 1206F and DW 1206J sold by Röhm & Haas.

The polyurethane polyethers that may be used according to the invention are in particular those described in the article by G. Fonnum, J. Bakke and Fk. Hansen—*Colloid Polym. Sci.,* 271, 380-389 (1993).

In one variant, use is made of a non-ionic associative polyurethane polyether able to be obtained by polycondensation of at least three compounds comprising (i) at least one polyethylene glycol comprising from 100 to 180 mol of ethylene oxide, (ii) a polyoxyethylenated stearyl alcohol comprising 100 mol of ethylene oxide and (iii) a diisocyanate.

Such a polymer is especially sold by Elementis under the name Rheolate FX 1100@, which is a polycondensate of polyethylene glycol containing 136 mol of ethylene oxide, of polyoxyethylenated stearyl alcohol with 100 mol of ethylene oxide and of hexamethylene diisocyanate (HDI) with a weight-average molecular weight (Mw) of 30 000 (INCI name: PEG-136/Steareth-100/HDI Copolymer).

According to another variant, use may also be made of a polyurethane polyether able to be obtained by polycondensation of at least three compounds comprising (i) at least one polyethylene glycol comprising from 150 to 180 mol of ethylene oxide, (ii) stearyl alcohol or decyl alcohol and (iii) at least one diisocyanate.

Such polyurethane polyethers are sold especially by Röhm & Haas under the names Aculyn 46 and Aculyn 44 [Aculyn 46 is a polycondensate of polyethylene glycol comprising 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44 is a polycondensate of polyethylene glycol (PEG) comprising 150 or 180 mol of ethylene oxide, of decyl alcohol and of methylenebis(4-cyclohexyl isocyanate) (SMDI), at 35% by weight in a mixture of propylene glycol (39%) and water (26%)].

Preferably, the associative polymers as described above have a number-average molecular weight of less than 500 000 and even more preferentially of less than 100 000, preferably ranging from 5000 to 80 000, which can be measured by methods such as cryoscopy, osmotic pressure, ebullioscopy or titration of the end groups.

The non-ionic associative polymer(s) according to the invention are preferably chosen from celluloses modified with groups comprising at least one fatty chain of family (1), in particular hydroxyethylcelluloses modified with groups comprising at least one fatty chain, such as alkyl, arylalkyl or alkylaryl groups, or mixtures thereof, and in which the alkyl groups are preferably $C_8$-$C_{22}$ alkyl groups, and polyurethane polyethers of family (7).

Preferentially, the non-ionic associative polymer used in the composition according to the invention is a non-ionic associative polymer chosen from the non-ionic associative polyurethane polyethers (family (7)), in particular those able to be obtained by polycondensation of at least three compounds comprising (i) at least one polyethylene glycol comprising from 150 to 180 mol of ethylene oxide, (ii) stearyl alcohol or decyl alcohol and (iii) at least one diisocyanate.

Even more particularly, the non-ionic associative polymer (s) used in the invention is (are) chosen from the polycondensate of polyethylene glycol comprising 150 or 180 mol of ethylene oxide, of decyl alcohol and of methylenebis(4-cyclohexyl isocyanate) (SMDI) sold under the name ACULYN 44, or the polycondensate of polyethylene glycol comprising 150 or 180 mol of ethylene oxide, of stearyl alcohol and of methylenebis(4-cyclohexyl isocyanate) (SMDI) sold under the name ACULYN 46, and mixtures thereof.

The composition according to the invention advantageously comprises the non-ionic associative polymer(s) used in a total amount preferably ranging from 0.01% to 5% by weight, better still from 0.05% to 2% by weight and even more preferentially ranging from 0.1% to 1% by weight relative to the total weight of the composition.

Preferentially, the composition according to the invention comprises the non-ionic associative polyurethane polyether (s) of family (7) in a total amount preferably ranging from 0.01% to 5% by weight, better still from 0.05% to 2% by weight, better still ranging from 0.1% to 1% by weight relative to the total weight of the composition.

D/ Non-Associative Polysaccharides

The composition according to the invention may advantageously comprise one or more non-associative polysaccharides, which are therefore different from the associative polymers above.

In the present invention, the term "polysaccharide" means a polymer constituted of sugar units. The term "sugar unit" means an oxygen-bearing hydrocarbon-based compound containing several alcohol functions, with or without aldehyde or ketone functions, and which includes at least 4 carbon atoms. The sugar units can be optionally modified by substitution, and/or by oxidation and/or by dehydration.

The sugar units that may be included in the composition of the polysaccharides of the invention are preferably derived from the following sugars: glucose, galactose, arabinose, rhamnose, mannose, xylose, fucose, anhydrogalactose, galacturonic acid, glucuronic acid, mannuronic acid, galactose sulfate, anhydrogalactose sulfate and fructose.

Non-associative polysaccharides that may in particular be mentioned include the following polymers, alone or as a mixture:

a) tree or shrub exudates, including:
   - acacia gum (branched polymer of galactose, arabinose, rhamnose and glucuronic acid);
   - ghatti gum (polymer derived from arabinose, galactose, mannose, xylose and glucuronic acid);
   - karaya gum (polymer derived from galacturonic acid, galactose, rhamnose and glucuronic acid);
   - gum tragacanth (or tragacanth) (polymer of galacturonic acid, galactose, fucose, xylose and arabinose);

b) gums derived from algae, including:
   - agar (polymer derived from galactose and anhydrogalactose);
   - alginates (polymers of mannuronic acid and of glucuronic acid);
   - carrageenans and furcellerans (polymers of galactose sulfate and of anhydrogalactose sulfate);

c) gums derived from seeds or tubers, including:
  guar gum (polymer of mannose and galactose);
  locust bean gum (polymer of mannose and galactose);
  fenugreek gum (polymer of mannose and galactose);
  tamarind gum (polymer of galactose, xylose and glucose);
  konjac gum (polymer of glucose and mannose);
d) microbial gums, including:
  xanthan gum (polymer of glucose, mannose acetate, mannose/pyruvic acid and glucuronic acid);
  gellan gum (polymer of partially acylated glucose, rhamnose and glucuronic acid);
  scleroglucan gum (glucose polymer);
e) polymers extracted from plants, including:
  celluloses (glucose polymers);
  starches (glucose polymers) and
  inulin.

These polymers can be physically or chemically modified. As physical treatment, mention may notably be made of a heat treatment. Mention may be made, as chemical treatments, of esterification, etherification, amidation or oxidation reactions. These treatments make it possible to produce polymers that may notably be non-ionic, anionic or amphoteric.

In particular, it is possible to modify/treat guar gums, locust bean gums, starches and celluloses.

The guar gums that may be used according to the invention can be modified with (poly)hydroxy($C_1$-$C_6$)alkyl groups. Mention may be made, by way of example, among the (poly)hydroxy($C_1$-$C_6$)alkyl groups, of the hydroxymethyl, hydroxyethyl, hydroxypropyl and hydroxybutyl groups. These guar gums are well known in the prior art and may be prepared, for example, by reacting corresponding alkene oxides, for instance propylene oxides, with the guar gum so as to obtain a guar gum modified with hydroxypropyl groups. The degree of hydroxyalkylation preferably ranges from 0.4 to 1.2 and corresponds to the number of alkylene oxide molecules consumed by the number of free hydroxyl functions present on the guar gum.

Such guar gums optionally modified with hydroxyalkyl groups are sold, for example, under the trade names Jaguar HP8, Jaguar HP60 and Jaguar HP120 by Rhodia Chimie.

The botanical origin of the starches that may be used in the present invention may be cereals or tubers. Thus, the starches are, for example, chosen from maize starch, rice starch, oat starch, cassava starch, barley starch, potato starch, wheat starch, sorghum starch, pea starch or tapioca starch. It is also possible to use hydrolysates of the starches mentioned above. The starch is preferably derived from potato.

Starch phosphates, in particular distarch phosphates or compounds rich in distarch phosphate will preferentially be used, for instance the product sold under the references Prejel VA-70-T AGGL (gelatinized hydroxypropyl cassava distarch phosphate), Prejel TK1 (gelatinized cassava distarch phosphate) or Prejel 200 (gelatinized acetyl cassava distarch phosphate) by the company Avebe, or Structure Zea from National Starch (gelatinized corn distarch phosphate).

According to the invention, use may also be made of amphoteric starches, these amphoteric starches comprising one or more anionic groups and one or more cationic groups. The anionic and cationic groups can be bonded to the same reactive site of the starch molecule or to different reactive sites; they are preferably bonded to the same reactive site. The anionic groups can be of carboxylic, phosphate or sulfate type and preferably carboxylic type. The cationic groups can be of primary, secondary, tertiary or quaternary amine type.

The polysaccharides that may be used according to the invention may be cellulose-based polymers.

The term “cellulose” polymer is understood to mean, according to the invention, any polysaccharide compound having, in its structure, sequences of glucose residues joined via β-1,4 bonds; in addition to unsubstituted celluloses, the cellulose derivatives can be anionic, cationic, amphoteric or non-ionic.

Thus, the cellulose polymers that may be used according to the invention may be chosen from unsubstituted celluloses, including those in a microcrystalline form, and cellulose ethers.

Among these cellulose-based polymers, cellulose ethers, cellulose esters and cellulose ether esters are distinguished.

The cellulose esters include cellulose inorganic esters (cellulose nitrates, sulfates, phosphates, and the like), cellulose organic esters (cellulose monoacetates, triacetates, amidopropionates, acetate butyrates, acetate propionates and acetate trimellitates, and the like), and mixed cellulose organic/inorganic esters, such as cellulose acetate butyrate sulfates and cellulose acetate propionate sulfates. Mention may be made, among the cellulose ether esters, of hydroxypropylmethylcellulose phthalates and ethylcellulose sulfates.

Among the cellulose ethers, mention may be made of ($C_1$-$C_4$)alkylcelluloses, such as methylcelluloses and ethylcelluloses (for example, Ethocel Standard 100 Premium from Dow Chemical); (poly)hydroxy($C_1$-$C_4$)alkylcelluloses, such as hydroxymethylcelluloses, hydroxyethylcelluloses (for example, Natrosol 250 HHR provided by Ashland) and hydroxypropylcelluloses (for example, Klucel EF from Aqualon); (poly)hydroxy($C_1$-$C_4$)alkyl($C_1$-$C_4$)alkylcellulose mixed celluloses, such as hydroxypropylmethylcelluloses (for example, Methocel E4M from Dow Chemical), hydroxyethylmethylcelluloses, hydroxyethylethylcelluloses (for example, Bermocoll E 481 FQ from AkzoNobel) and hydroxybutylmethylcelluloses.

Among the anionic cellulose ethers, mention may be made of (poly)carboxy($C_1$-$C_4$)alkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and the sodium salts thereof.

Among the cationic cellulose ethers, mention may be made of cationic cellulose derivatives such as cellulose copolymers or cellulose derivatives grafted with a water-soluble quaternary ammonium monomer, and described in particular in patent U.S. Pat. No. 4,131,576, such as (poly)hydroxy($C_1$-$C_4$)alkyl celluloses, for instance hydroxymethyl-, hydroxyethyl- or hydroxypropylcelluloses grafted notably with a methacryloylethyltrimethylammonium, methacrylamidopropyltrimethylammonium or dimethyldiallylammonium salt. The commercial products corresponding to this definition are more particularly the products sold under the names “Celquat® L 200” and “Celquat® H 100” by the company National Starch.

Preferably, the non-associative polysaccharide(s) are chosen from, alone or as a mixture, celluloses and starches, which are native or modified for example by a heat treatment, an esterification reaction, an etherification reaction, an etherification reaction, an amidation reaction or an oxidation reaction; preferentially starches. Better still, the non-associative polysaccharides are chosen from, alone or as a mixture, starch phosphates, in particular distarch phosphates, and amphoteric starches; preferentially from starch phosphates, in particular distarch phosphates.

Preferably, when they are present, the composition according to the invention comprises the non-associative polysaccharide(s) in a total amount ranging from 0.1% to 15% by weight, preferably from 0.5% to 10% by weight and even better still from 1% to 5% by weight, relative to the total weight of the composition according to the invention.

Preferentially, the composition according to the invention may comprise the non-associative polysaccharide(s) chosen from celluloses and/or starches in a total amount ranging from 0.1% to 15% by weight, preferably from 0.5% to 10% by weight, and even better from 1% to 5% by weight, relative to the total weight of the composition according to the invention.

More preferentially, the composition according to the invention may comprise the non-associative polysaccharide (s) chosen from starches in a total amount ranging from 0.1% to 15% by weight, preferably from 0.5% to 10% by weight, and even better still from 1% to 5% by weight, relative to the total weight of the composition according to the invention.

E/ Polyols

The composition according to the invention can also comprise one or more polyols.

They can in particular be of formula R—OH, in which R is a linear or branched, saturated or unsaturated hydrocarbon-based radical comprising at least one OH radical.

Preferably, said polyol(s) are linear and saturated; they may comprise from 2 to 6 hydroxyl OH radicals, in particular from 2 to 4, better still 3 OH radicals. They may comprise from 2 to 8 carbon atoms and notably from 2 to 6 carbon atoms.

Thus, R is advantageously a linear and saturated hydrocarbon-based radical comprising 2 to 8, better still 2 to 6, carbon atoms, and 1 to 5, better still 1 to 3, even better still 2, OH radicals.

The polyols do not comprise oxyalkylenated or glycerolated groups. They are advantageously liquid at ambient temperature (25° C.) and atmospheric pressure (1 atm).

Preferably, the polyols according to the invention are linear and saturated and comprise 2 or 3 OH groups (diols or triols) and 2 to 6 carbon atoms.

Preferentially, they may be chosen from propylene glycol (propane-1,2-diol), propane-1,3-diol, butylene glycol (butane-1,3-diol), pentylene glycol (pentane-1,2-diol), glycerol, and mixtures thereof. Very preferably, the polyol is glycerol.

When they are present, the composition according to the invention may comprise said polyol(s) in a total amount greater than or equal to 3% by weight relative to the total weight of the composition.

Preferably, the composition according to the invention comprises said polyol(s) in a total amount ranging from 3.0% to 20% by weight, better still from 3.5% to 15% by weight, or even from 4.0% to 10% by weight, preferentially from 4.0% to 8.0% by weight, relative to the total weight of the composition.

The composition according to the invention preferentially comprises glycerol in an amount ranging from 3.0% to 20% by weight, better still from 3.5% to 15% by weight, or even 4.0% to 10% by weight, preferentially from 4.0% to 8.0% by weight, relative to the total weight of the composition.

F/ Solid Fatty Alcohol

Preferably, the composition according to the invention also comprises one or more solid fatty alcohols, in particular comprising 8 to 30 carbon atoms.

The term "solid fatty alcohol" is intended to mean a fatty alcohol which is solid at 25° C. and 1 atm. They are advantageously non-glycerolated and non-oxyalkylenated.

They preferably correspond to the formula R—OH in which R is a linear or branched, saturated or unsaturated hydrocarbon-based radical comprising 8 to 30 carbon atoms, optionally comprising one or more OH groups.

Preferably, R comprises from 10 to 22 carbon atoms, or even from 12 to 20 carbon atoms.

Preferably, R is a linear or branched, saturated radical, better still a saturated linear radical.

Preferentially, R is a saturated linear radical comprising from 8 to 30 carbon atoms, better still from 10 to 22 carbon atoms, even better still from 12 to 20 carbon atoms, and not comprising a hydroxyl group.

The solid fatty alcohols that may be used are preferably chosen from linear or branched, saturated or unsaturated, preferably saturated and linear, alcohols comprising from 8 to 30 carbon atoms, better still from 10 to 22 carbon atoms, even better still from 12 to 20 carbon atoms, and advantageously not comprising a hydroxyl group. Mention may be made of myristyl alcohol, cetyl alcohol and stearyl alcohol and the mixture thereof, namely cetylstearyl alcohol.

Preferably, the composition comprises one or more solid fatty alcohols notably chosen from myristyl alcohol, cetyl alcohol, stearyl alcohol and cetylstearyl alcohol.

Preferably, when they are present, the composition according to the invention comprises the solid fatty alcohol (s) in a total content of between 0.5% and 15% by weight, better still between 1% and 10% by weight, preferentially between 2% and 5% by weight, relative to the total weight of the composition.

G/ Cationic Surfactants

Preferably, the composition according to the invention comprises one or more cationic surfactants.

The term "cationic surfactant" is intended to mean a surfactant that is positively charged when it is contained in the composition according to the invention. This surfactant may bear one or more positive permanent charges or may contain one or more cationizable functions in the composition according to the invention.

The cationic surfactant(s) can be chosen from primary, secondary or tertiary fatty amines, which are optionally polyoxyalkylenated, or salts thereof, quaternary ammonium salts, and mixtures thereof. The fatty amines generally comprise at least one $C_8$-$C_{30}$ hydrocarbon-based chain.

The cationic surfactant(s) are preferably chosen from quaternary ammonium salts, among which mention may be made of:

(i) the compounds corresponding to general formula (I):

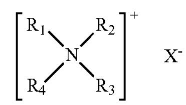

in which the groups $R_1$ to $R_4$, which may be identical or different, represent a linear or branched aliphatic group including from 1 to 30 carbon atoms, or an aromatic group such as aryl or alkylaryl, at least one of the groups $R_1$ to $R_4$ denoting a linear or branched aliphatic radical comprising from 8 to 30 carbon atoms and preferably from 12 to 24 carbon atoms, it being possible for the aliphatic groups to include heteroatoms notably such as oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates and ($C_1$-$C_4$)alkylsulfonates or ($C_1$-$C_4$)alkylarylsulfonates.

Among the quaternary ammonium salts of formula (I), the ones that are preferred are, on the one hand, tetraalkylammonium salts, for instance dialkyldimethylammonium or alkyltrimethylammonium salts in which the alkyl group comprises approximately from 12 to 22 carbon atoms, in particular behenyltrimethylammonium, distearyldimethylammonium, cetyltrimethylammonium or benzyldimethylstearylammonium salts, or else, on the other hand, the palmitylamidopropyltrimethylammonium salts, the stearamidopropyltrimethylammonium salts, the stearamidopropyldimethylcetearylammonium salts, or the stearamidopropyldimethyl(myristyl acetate)ammonium salts sold under the name Ceraphyl® 70 by the company Van Dyk. It is preferred in particular to use the chloride salts of these compounds;

(ii) quaternary ammonium salts of imidazoline, such as those of formula (II):

(II)

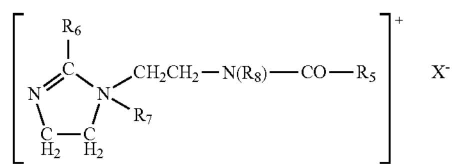

in which $R_5$ represents an alkenyl or alkyl group comprising from 8 to 30 carbon atoms, for example derived from tallow fatty acids, $R_6$ represents a hydrogen atom, a $C_1$-$C_4$ alkyl group or an alkenyl or alkyl group comprising from 8 to 30 carbon atoms, $R_7$ represents a $C_1$-$C_4$ alkyl group, $R_8$ represents a hydrogen atom or a $C_1$-$C_4$ alkyl group and $X^-$ is an anion chosen from the group of the halides, phosphates, acetates, lactates, alkyl sulfates, alkylsulfonates or alkylarylsulfonates, the alkyl and aryl groups of which preferably comprise, respectively, from 1 to 20 carbon atoms and from 6 to 30 carbon atoms.

Preferably, $R_5$ and $R_6$ denote a mixture of alkenyl or alkyl groups including from 12 to 21 carbon atoms, for example derived from tallow fatty acids, $R_7$ denotes a methyl group and $R_8$ denotes a hydrogen atom.

Such a product is for example sold under the name Rewoquat® W 75 by the company Rewo; among the compounds of formula (II), mention may also be made of the product sold under the name Varisoft W 575 PG N by the company Evonik Goldschmidt:

(iii) diquaternary or triquaternary ammonium salts of formula (III):

(III)

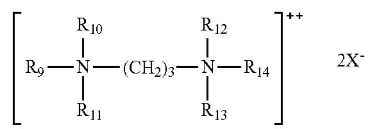

in which $R_9$ denotes an alkyl radical comprising approximately from 16 to 30 carbon atoms, which is optionally hydroxylated and/or optionally interrupted with one or more oxygen atoms, $R_{10}$ is chosen from hydrogen or an alkyl radical comprising from 1 to 4 carbon atoms or a group $(R_{9a})(R_{10a})(R_{11a})N—(CH_2)_3$, $R_{9a}$, $R_{10a}$, $R_{11a}$, $R_{11}$, $R_{12}$, $R_{13}$ and $R_{14}$, which may be identical or different, are chosen from hydrogen or an alkyl radical comprising from 1 to 4 carbon atoms, and $X^-$ is an anion chosen from the group of halides, acetates, phosphates, nitrates, ($C_1$-$C_4$)alkyl sulfates, ($C_1$-$C_4$)alkyl sulfonates and ($C_1$-$C_4$)alkylaryl sulfonates, and in particular methyl sulfate and ethyl sulfate.

Such compounds are, for example, Finquat CT-P, sold by the company FINETEX (Quaternium 89), and Finquat CT, sold by the company FINETEX (Quaternium 75); (iv) quaternary ammonium salts comprising at least one ester function, such as those of formula (IV):

(IV)

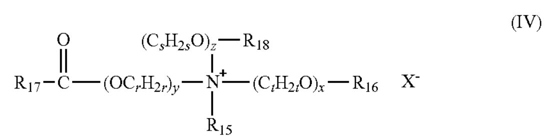

in which:

$R_{15}$ is chosen from $C_1$-$C_6$ alkyl groups and $C_1$-$C_6$ hydroxyalkyl or dihydroxyalkyl groups;

$R_{16}$ is chosen from the $R_{20}$ groups which are linear or branched, saturated or unsaturated $C_1$-$C_{22}$ hydrocarbon-based groups; a hydrogen atom; and the group $R_{19}$—C(O)—;

$R_{18}$ is chosen from the group $R_{21}$—C(O)—; the $R_{22}$ groups which are linear or branched, saturated or unsaturated $C_1$-$C_6$ hydrocarbon-based groups; a hydrogen atom;

$R_{17}$, $R_{19}$ and $R_{21}$, which may be identical or different, are chosen from linear or branched, saturated or unsaturated $C_7$-$C_{21}$ hydrocarbon-based groups;

r, s and t, which may be identical or different, are integers having a value of 2 to 6; y is an integer having a value from 1 to 10; x and z, which may be identical or different, are integers having a value from 0 to 10;

$X^-$ is a simple or complex, organic or mineral anion;

with the proviso that the sum x+y+z is from 1 to 15, that when x is 0 then $R_{16}$ denotes $R_{20}$, and that when z is 0 then $R_{18}$ denotes $R_{22}$.

The alkyl groups $R_{15}$ may be linear or branched, and more particularly linear.

Preferably, $R_{15}$ denotes a methyl, ethyl, hydroxyethyl or dihydroxypropyl group, and more particularly a methyl or ethyl group.

Advantageously, the sum x+y+z is from 1 to 10.

When $R_{16}$ is a hydrocarbon-based group $R_{20}$, it may be long and contain from 12 to 22 carbon atoms, or short and contain from 1 to 3 carbon atoms.

When $R_{18}$ is a hydrocarbon-based group $R_{22}$, it preferably contains 1 to 3 carbon atoms. Advantageously, $R_{17}$, $R_{18}$ and $R_{21}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion that is compatible with the ammonium bearing an ester function.

The anion $X^-$ is even more particularly chloride or methyl sulfate.

Use may be made more particularly in the composition according to the invention of the ammonium salts of formula (IV) in which:

$R_{15}$ denotes a methyl or ethyl group, x and y are equal to 1; z is equal to 0 or 1; r, s and t are equal to 2;

$R_{16}$ is chosen from the group $R_{19}$—C(O)—; methyl, ethyl or $C_{14}$-$C_{22}$ hydrocarbon-based groups; a hydrogen atom;

$R_{18}$ is chosen from the group $R_{21}$—C(O)—; a hydrogen atom;

$R_{17}$, $R_{19}$ and $R_{21}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Examples that may be mentioned include the compounds of formula (IV) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by a quaternization using an alkylating agent such as an alkyl halide (preferably a methyl or ethyl halide), a dialkyl sulfate (preferably a methyl or ethyl sulfate), methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in patents U.S. Pat. Nos. 4,874,554 and 4,137,180.

Use may be made of behenoylhydroxypropyltrimethylammonium chloride made available by KAO under the name Quatarmin BTC 131.

Preferably, the ammonium salts containing at least one ester function contain two ester functions.

Among the quaternary ammonium salts containing at least one ester function that may be used, it is preferred to use dipalmitoylethylhydroxyethylmethylammonium salts.

The cationic surfactant(s) are preferably chosen from those of formula (I) and those of formula (II) and even more preferentially from those of formula (I).

Preferentially, the cationic surfactant(s) are chosen from those of formula (I), more preferentially from behenyltrimethylammonium salts, cetyltrimethylammonium salts, and a mixture of these compounds, and even more preferentially from behenyltrimethylammonium chloride, cetyltrimethylammonium chloride, and a mixture of these compounds.

Preferably, the composition according to the invention comprises the cationic surfactant(s) in a total content ranging from 0.1% to 10% by weight, preferentially from 0.5% to 8% by weight and even better still from 1% to 5% by weight, relative to the total weight of the composition.

The composition according to the invention advantageously comprises water, in particular at a concentration preferably ranging from 70% to 98% by weight, in particular from 75% to 95% by weight and better still from 80% to 90% by weight, relative to the total weight of the composition.

The composition according to the invention may also comprise at least one or more common cosmetic ingredients other than the compounds described above, in particular chosen from thickeners, gelling agents; sunscreens; moisturizers; antidandruff agents; antioxidants; chelating agents; reducing agents; oxidation bases, couplers, oxidizing agents, direct dyes; hair-relaxing agents; nacreous agents and opacifiers; micas, nacres, glitter flakes; plasticizers or coalescence agents; hydroxy acids; pigments; fillers; fragrances; basifying or acidifying agents; silanes. A person skilled in the art will take care to select the ingredients included in the composition, and also the amounts thereof, so that they do not harm the properties of the compositions of the present invention.

The cosmetic composition according to the invention especially finds a particularly advantageous application in the hair sector, especially for caring for and/or conditioning the hair. The hair compositions are preferably leave-on or rinse-off hair conditioners or hair masks; advantageously, the composition according to the invention in the form of a hair mask.

The cosmetic composition may or may not be rinsed off after having been applied to the keratin materials, in particular the hair, over the entire head of hair or on the ends only for example. It is preferably rinsed off with water, after an optional leave-on time. It is possible for it to not be rinsed off, for example when applied to the ends of the hair.

A subject of the invention is also a process for cosmetic treatment, in particular cosmetic hair treatment, in particular for caring for and/or conditioning keratin materials, in particular the hair, comprising the application to said keratin materials of a composition as defined above.

Said application step may or may not be followed by a rinsing step, after an optional leave-on time, and/or a drying step. Preferably, it is followed by a rinsing step, after an optional leave-on time, and/or a drying step.

The present invention is illustrated in greater detail in the examples that follow (% AM=% of active material in the composition).

EXAMPLE 1

The hair compositions according to the invention below were prepared, said compositions comprising (% by weight of AM):

TABLE 1

| | Composition A | Composition B |
|---|---|---|
| Non-ionic emulsion of silicone and amino silicone (Example 1 from WO 2017/108824) | 1.08% AM of PDMS + 0.27% AM of amodimethicone | 1.08% AM of PDMS + 0.27% AM of amodimethicone |
| PEG-150/decyl alcohol/SMDI copolymer (Aculyn 44) | 0.2 | 0.2 |
| Distarch phosphate | 1.5 | 1.5 |
| Glycerol | 5 | 5 |
| Propylene glycol | 0.6 | 0.6 |
| Behentrimonium chloride | 0.8 | 0.8 |
| Quaternium-87 | 1.2 | 1.2 |
| Cetearyl alcohol | 3.5 | 3.5 |
| 2-Oleamido-1,3-octadecanediol | — | 0.01 |
| *Cocos nucifera* (coconut) oil | — | 0.01 |
| Preservatives | q.s. | q.s. |
| Water | q.s. 100 | q.s. 100 |

Hair care compositions are obtained in the form of a smooth, shiny cream, having a soft, light and fine texture.

The compositions are easily spread over the head of hair and "melt" there quickly, leading to rapid and easy absorption of the product into the head of hair.

They rinse off quickly; after rinsing, the hair disentangles easily, and is very soft and smooth to the touch.

EXAMPLE 2

The following hair compositions were prepared, comprising (in g % of active matter AM)

TABLE 2

| | A1 Invention | B1 Comparative |
|---|---|---|
| Silicone emulsion (PDMS + amodimethicone, with nonionic surfactants) (ex 1 of WO2017/108824) | 1.08% AM PDMS + 0.27% AM amodimethicone | 1.08% AM PDMS + 0.27% AM amodimethicone |
| PEG-150/DECYL ALCOHOL/SMDI COPOLYMER (35% AM, comprises 60/40 propylene glycol/water) (Aculyn 44) | 0.2 AM (+0.2% AM PPG) | — |
| Propylene glycol | — | 0.2 AM |
| DISTARCH PHOSPHATE | 1.5 | 1.5 |
| Glycerol | 3.4 | 3.4 |
| Behentrimonium Chloride | 0.8 AM | 0.8 AM |
| QUATERNIUM-87 (75% AM and 25% AM propylene glycol) | 1.2 AM (+0.4 AM PPG) | 1.2 AM (+0.4 AM PPG) |
| CETEARYL ALCOHOL | 3.5 | 3.5 |
| Preservatives | Qs | Qs |
| Water | Qsp 100 | Qsp 100 |
| Total amount of polyols | 4 | 4 |

Hair care compositions are obtained in the form of a cream.

The shine (glossiness) of the cream was evaluated blindly by 4 experts, who gave a score ranging from 0 (very low shine) to 5 (high shine), in steps of 0.5.

The evaluation is done visually, in daylight. The expert takes each jar and evaluates the shine by observing the appearance of the cream during oscillating movements back and forth.

Below are the results obtained:

TABLE 3

| | A1 Invention | B1 Comparative |
|---|---|---|
| Expert 1 | 4 | 4 |
| Expert 2 | 4 | 3.5 |
| Expert 3 | 4 | 2.5 |
| Expert 4 | 4 | 3 |
| Average | 4 | 3.25 |
| Standard deviation | 0.00 | 0.65 |

The composition A1 according to the invention has a more shiny (more glossy) appearance compared to the comparative composition B1.

The invention claimed is:

1. A composition comprising:

(i) an oil-in-water emulsion comprising:

(a) at least one amino silicone, (b) at least one non-amino silicone, and (ii) at least one non-ionic associative polymer chosen from polyurethane polyethers able to be obtained by polycondensation of at least three compounds comprising:

(a) at least one polyethylene glycol, (b) at least one alcohol, and (c) at least one diisocyanate.

2. The composition of claim 1, wherein the at least one amino silicone is chosen from:

A) polysiloxanes of formula (I):

(I)

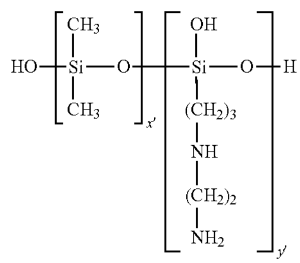

wherein x' and y' represent integers such that the weight-average molecular weight (Mw) of the polysiloxanes of formula (I) ranges from 5000 to 500 000 g/mol;

B) amino silicones of formula (II):

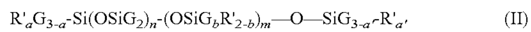

$R'_aG_{3-a}$-Si($OSiG_2$)$_n$-($OSiG_bR'_{2-b}$)$_m$—O—$SiG_{3-a'}$-$R'_{a'}$ (II)

wherein:

G is chosen from a hydrogen atom, a phenyl, an OH group, or a $C_1$-$C_8$ alkyl group, a and a' are independently chosen from 0 or an integer ranging from 1 to 3, wherein at least one of a and a' is equal to zero, b represents 0 or 1, m and n represent integers such that the sum (n+m) ranges from 1 to 2000; and R' is chosen from a monovalent radical of formula —$C_qH_{2q}$L, wherein q represents an integer ranging from 2 to 8, and L is an optionally quaternized amino group chosen from: —NR"-Q-N(R")$_2$, —N(R")$_2$, —$N^+$(R")$_3$ A−, —$N^+$H(R")$_2$ $A^-$, —$N^+$H2(R") $A^-$, —NR"-Q-$N^+$(R")$H_2$ $A^-$, —NR"-Q-$N^+$(R")$_2$H $A^-$, or —NR"-Q-$N^+$(R")$_3$ $A^-$, wherein R" is chosen from hydrogen, a phenyl group, a benzyl group, or a monovalent saturated hydrocarbon-based radical; Q represents a linear or branched group of formula $C_rH_{2r}$, wherein r represents an integer ranging from 2 to 6; and $A^-$ represents a cosmetically acceptable anion;

C) amino silicones of formula (VIII):

(VIII)

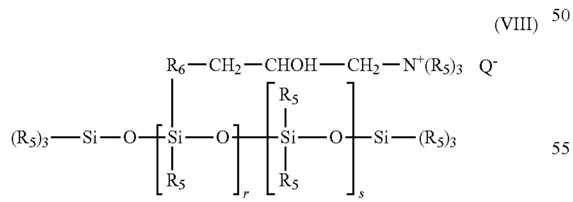

wherein:

$R_5$ represents a monovalent hydrocarbon-based radical comprising from 1 to 18 carbon atoms;

$R_6$ represents a divalent hydrocarbon-based radical;

$Q^-$ represents an anion;

r represents a mean statistical value ranging from 2 to 20; and s represents a mean statistical value ranging from 20 to 200;

D) quaternary ammonium silicones of formula (IX):

(IX)

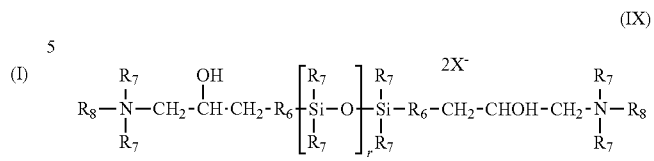

wherein:

$R_7$ is chosen from a monovalent hydrocarbon-based radical comprising from 1 to 18 carbon atoms;

$R_6$ represents a divalent hydrocarbon-based radical;

$R_8$ is chosen from a hydrogen atom or a monovalent hydrocarbon-based radical comprising from 1 to 18 carbon atoms;

$X^-$ represents an anion; and r represents a mean statistical value ranging from 2 to 200;

E) amino silicones of formula (X):

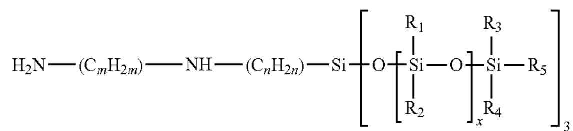

wherein:

$R_1$, $R_2$, $R_3$, and $R_4$ are independently chosen from a $C_1$-$C_4$ alkyl radical or a phenyl group, $R_5$ represents a $C_1$-$C_4$ alkyl radical or a hydroxyl group, n represents an integer ranging from 1 to 5, m represents an integer ranging from 1 to 5, and x is chosen such that the amine number ranges from 0.01 to 1 meq/g;

F) multiblock polyoxyalkylenated amino silicones, of the type $(AB)_n$, wherein A represents a polysiloxane block, and B represents a polyoxyalkylenated block comprising at least one amine group;

G) amino silicones of formulas (XI) or (XII):

(XI)

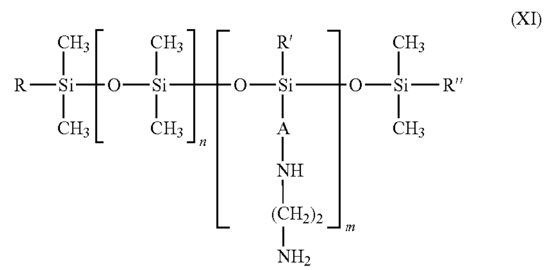

wherein:

R, R', and R" are independently chosen from a $C_1$-$C_4$ alkyl group or a hydroxyl group, A represents a $C_3$ alkylene radical; and m and n represent integers such that the weight-average molecular weight of the amino silicones of formula (XI) ranges from 5000 to 500,000;

(XII)

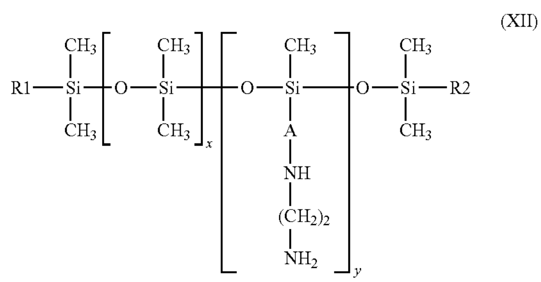

wherein:

x and y represent integers ranging from 1 to 5000;

$R_1$ and $R_2$ are independently chosen from a linear or branched, saturated or unsaturated alkyl group comprising from 6 to 30 carbon atoms; and A represents a linear or branched alkylene radical comprising from 2 to 8 carbon atoms;

H) polysiloxanes; or

I) mixtures of two or more thereof.

3. The composition of claim 2, wherein the amino silicones of formula (II) are chosen from:

(a) “trimethylsilylamodimethicone” silicones of formula (III):

(III)

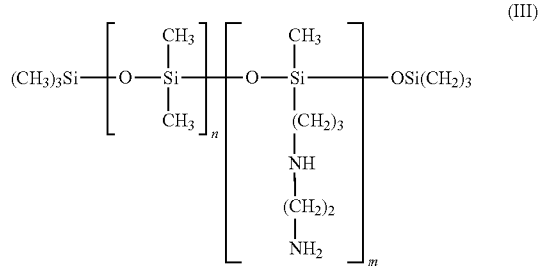

wherein m and n represent integers such that the sum (n+m) ranges from 1 to 2000;

(b) silicones of formula (IV):

(IV)

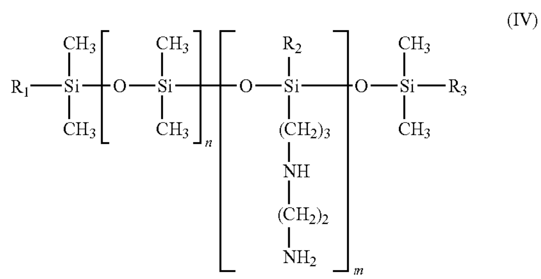

wherein:

m and n represent integers such that the sum (n+m) ranges from 1 to 1000; and $R_1$, $R_2$, and $R_3$ are independently chosen from a hydroxyl or $C_1$-$C_4$ alkoxy radical, wherein at least one of $R_1$, $R_2$, or $R_3$ represents an alkoxy radical;

(c) silicones of formula (V):

(V)

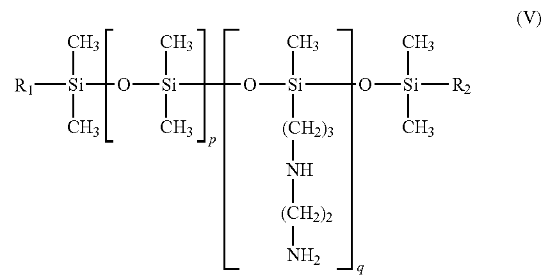

wherein:

p and q are integers such that the sum (p+q) ranges from 1 to 1000; and $R_1$ and $R_2$ are independently chosen from a hydroxyl or a $C_1$-$C_4$ alkoxy radical, wherein at least one of the radicals $R_1$ or $R_2$ represents an alkoxy radical;

(d) silicones of formula (VI):

(VI)

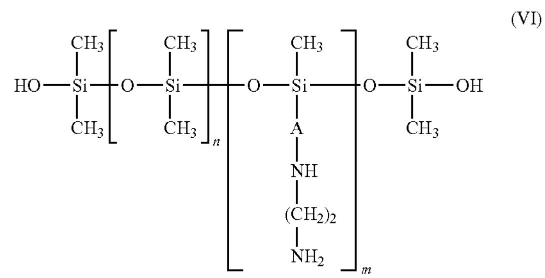

wherein:

m and n represent integers such that the sum (n+m) ranges from 1 to 2000; and represents a linear or branched alkylene radical comprising from 4 to 8 carbon atoms;

(e) silicones of formula (VII):

(VII)

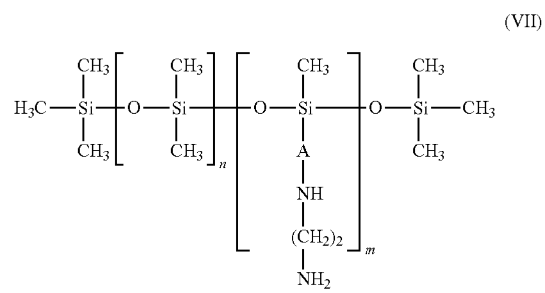

wherein:

m and n represent integers such that the sum (n+m) ranges from 1 to 2000; and

A represents a linear or branched alkylene radical comprising from 4 to 8 carbon atoms.

4. The composition of claim 2, wherein the polysiloxanes are chosen from formulas (XIV), (XV) or (XVI):

(XIV)

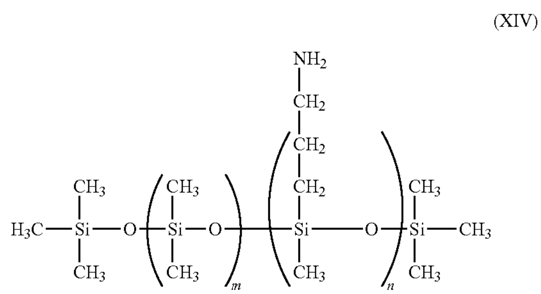

wherein the values of n and m are integers wherein the weight-average molecular weight of the amino silicone of formula (XIV) ranges from 1000 to 55,000;

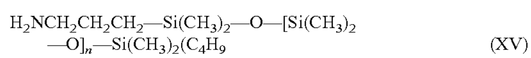

$H_2NCH_2CH_2CH_2—Si(CH_3)_2—O—[Si(CH_3)_2—O]_n—Si(CH_3)_2(C_4H_9)$ (XV)

wherein the value of n is an integer wherein the weight-average molecular weight of the amino silicone of formula (XV) ranges from 500 to 3000; and (XVI)

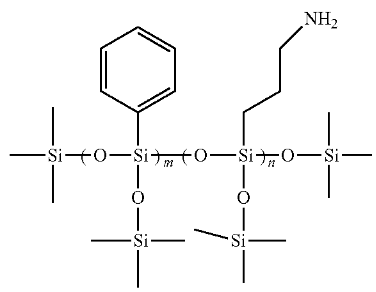

wherein wherein the values of n and m are integers wherein the weight-average molecular weight of the amino silicone of formula (XVI) ranges from 500 to 50,000.

5. The composition of claim 1, wherein the total amount of amino silicone(s) ranges from 0.01% to 5% by weight, relative to the total weight of the composition.

6. The composition of claim 1, wherein the at least one non-amino silicone is chosen from:

polydialkylsiloxanes; or non-amino organopolysiloxanes.

7. The composition of claim 6, wherein the polydialkysiloxanes are chosen from polydimethylsiloxanes, polydiarylsiloxanes, polyalkylarylsiloxanes, silicone gums, silicone resins, or mixtures of two or more thereof.

8. The composition of claim 6, wherein the non-amino organopolysiloxanes are chosen from organopolysiloxanes chosen from polyoxyethylene optionally comprising $C_6$-$C_{24}$ alkyl groups, polyoxypropylene groups optionally comprising $C_6$-$C_{24}$ alkyl groups, thiol groups, alkoxylated groups, hydroxyl groups, acyloxyalkyl groups, anionic groups of the carboxylic acid type, or mixtures of two or more thereof.

9. The composition of claim 1, wherein the total amount of non-amino silicone(s) ranges from 0.1% to 10% by weight, relative to the total weight of the composition.

10. The composition of claim 1, wherein the oil-in-water emulsion has a particle size D50 of less than 350 nm, and comprises:

a silicone mixture comprising a polydialkylsiloxane comprising (i) trialkylsilyl end groups with a viscosity at 25° C. ranging from 40,000 to 100,000 mPa·s, and (ii) an amino silicone with a viscosity at 25° C. ranging from 1000 to 15,000 mPa·s and an amine number ranging from 2 to 10 mg of KOH per gram of amino silicone;

a surfactant mixture comprising one or more non-ionic surfactants with an HLB ranging from 10 to 16, and water.

11. The composition of claim 1, wherein the total amount of oil-in-water emulsion ranges from 0.1% to 10% by weight, relative to the total weight of the emulsion.

12. The composition of claim 1, wherein (i) the at least one polyethylene glycol comprises from 150 to 180 mol of ethylene oxide, and (ii) the at least one alcohol is stearyl alcohol or decyl alcohol.

13. The composition of claim 1, wherein the total amount of non-ionic associative polymer(s) ranges from 0.01% to 5% by weight, relative to the total weight of the composition.

14. The composition of claim 1, further comprising at least one non-associative polysaccharide.

15. The composition of claim 14, wherein the at least one non-associative polysaccharide is chosen from:

a) tree or shrub exudates chosen from acacia gum; ghatti gum; karaya gum; or gum tragacanth;

b) gums derived from algae chosen from agar; alginates; carrageenans, or furcellerans;

c) gums derived from seeds or tubers chosen from guar gum; locust bean gum; fenugreek gum; tamarind gum; or konjac gum;

d) microbial gums chosen from xanthan gum; gellan gum; or scleroglucan gum;

e) polymers extracted from plants chosen from celluloses; starches; or inulin;

f) mixtures of two or more thereof.

16. The composition of claim 1, further comprising at least one polyol, at least one solid fatty alcohol, and at least one cationic surfactant.

17. The composition of claim 1, further comprising water, wherein the total amount of water ranges from 70 to 98% by weight, relative to the total weight of the composition.

18. A composition comprising:

(i) an oil-in-water emulsion having a particle size D50 of less than 350 nm, and comprising:

a silicone mixture comprising (a) a polydialkylsiloxane comprising trialkylsilyl end groups, having a viscosity at 25° C. ranging from 40,000 to 100,000 mPa·s, and (b) an amino silicone having a viscosity at 25° C. ranging from 1,000 to 15,000 mPa·s and an amine number ranging from 2 to 10 mg of KOH per gram of amino silicone;

a surfactant mixture comprising one or more non-ionic surfactants, said mixture having an HLB ranging from 10 to 16; and water; and (ii) at least one non-ionic associative polymer chosen from:

a polycondensate of polyethylene glycol comprising 150 or 180 mol of ethylene oxide, of decyl alcohol and of methylenebis(4-cyclohexyl isocyanate) (SMDI), or a polycondensate of polyethylene glycol comprising 150 or 180 mol of ethylene oxide, of stearyl alcohol and of methylenebis(4-cyclohexyl isocyanate) (SMDI), or mixtures thereof.

19. A method for treating keratin materials, comprising applying to said keratin materials a composition comprising:

(i) an oil-in-water emulsion comprising:
(a) at least one amino silicone,
(b) at least one non-amino silicone, and
(ii) at least one non-ionic associative polymer chosen from polyurethane polyethers able to be obtained by Polycondensation of at least three compounds comprising:
(a) at least one polyethylene glycol,
(b) at least one alcohol, and
(c) at least one diisocyanate.

* * * * *